US008287863B2

(12) United States Patent
Kosaka et al.

(10) Patent No.: US 8,287,863 B2
(45) Date of Patent: *Oct. 16, 2012

(54) METHOD FOR TREATING MYELOMA UTILIZING AN EXPRESSION ENHANCER FOR HM1.24 ANTIGEN

(75) Inventors: Masaaki Kosaka, Tokushima (JP); Shuji Ozaki, Tokushima (JP); Yuji Wakahara, Gotemba (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 28 days.

This patent is subject to a terminal disclaimer.

(21) Appl. No.: 11/402,927

(22) Filed: Apr. 13, 2006

(65) Prior Publication Data
US 2006/0193828 A1 Aug. 31, 2006

Related U.S. Application Data

(63) Continuation of application No. 10/069,290, filed as application No. PCT/JP00/05617 on Aug. 22, 2000, now abandoned.

(30) Foreign Application Priority Data

Aug. 23, 1999 (JP) .................................... 11-236007
Feb. 16, 2000 (JP) .................................. 2000-38689

(51) Int. Cl.
A61K 38/21 (2006.01)
A61K 38/00 (2006.01)
A61K 39/395 (2006.01)
(52) U.S. Cl. ................. 424/133.1; 424/85.6; 424/155.1; 514/1.1; 514/19.3
(58) Field of Classification Search ........................ None
See application file for complete search history.

(56) References Cited

U.S. PATENT DOCUMENTS

| 4,401,756 | A | 8/1983 | Gillis |
| 5,328,989 | A | 7/1994 | Vellekamp et al. |
| 5,756,318 | A | 5/1998 | Kosuna |
| 5,830,463 | A | 11/1998 | Duke et al. |
| 6,180,370 | B1 | 1/2001 | Queen et al. |
| 6,258,352 | B1 | 7/2001 | Shimonaka |
| 6,503,510 | B2 | 1/2003 | Koishihara et al. |
| 7,931,897 | B2 | 4/2011 | Kosaka et al. |
| 2002/0037288 | A1 | 3/2002 | Koishihara et al. |
| 2003/0175281 | A1 | 9/2003 | Kosaka et al. |
| 2006/0078539 | A1 | 4/2006 | Kosaka et al. |
| 2011/0223133 | A1 | 9/2011 | Kosaka et al. |

FOREIGN PATENT DOCUMENTS

| EP | 0 125 023 | 11/1984 |
| EP | 0 239-400 | 9/1987 |
| EP | 0 256 714 | 2/1988 |
| EP | 0 733 643 | 9/1996 |
| EP | 0 770 628 | 5/1997 |
| EP | 0 960 936 | 12/1999 |
| EP | 0 997 152 | 5/2000 |
| JP | 7-196694 | 1/1995 |
| JP | 7-236475 | 9/1995 |
| WO | WO-83/04313 | 12/1983 |
| WO | WO-92/01047 | 1/1992 |
| WO | WO-92/03918 | 3/1992 |
| WO | WO-92/20791 | 11/1992 |
| WO | WO-93/06213 | 4/1993 |
| WO | WO-93/11236 | 6/1993 |
| WO | WO-93/12227 | 6/1993 |
| WO | WO-93/19172 | 9/1993 |
| WO | WO-94/02602 | 2/1994 |
| WO | WO-94/06818 | 3/1994 |
| WO | WO-94/11523 | 5/1994 |
| WO | WO-94/25585 | 11/1994 |
| WO | WO-95/01438 | 1/1995 |
| WO | WO-95/15388 | 6/1995 |
| WO | WO-96/02576 | 2/1996 |
| WO | WO-96/04925 | 2/1996 |
| WO | WO-96/30394 | 3/1996 |
| WO | WO-96/33735 | 10/1996 |
| WO | WO-96/34096 | 10/1996 |
| WO | WO-98/14580 | 4/1998 |
| WO | WO-98/35698 | 8/1998 |
| WO | WO99/18997 | 4/1999 |
| WO | WO-01/13940 | 3/2001 |
| WO | WO-01/97844 | 12/2001 |

OTHER PUBLICATIONS

Arora et al. (1998) Differential Myeloma Cell Responsiveness to Interferon-Alpha Correlates with Differential Induction of p19INK4d and Cyclin D2 Expression JBC 273(19), pp. 11799-11805.
Australian Office Action dated May 18, 2004.
Australian Office Action mailed Apr. 1, 2005, directed to counterpart foreign application.
Birnbaum et al., "Phosphorylation of the Oncogenic Transcription Factor Interferon Regulatory Factor 2 (IRF2) In Vitro and In Vivo", Journal of Cellular Biochemistry 66 (1997) pp. 175-183.
Bungard et al., (1998) "The Combination of IL-2 and IFN Alpha Effectively Augments the Antibody-Dependent Cellular Cytotoxicity of Monoclonal Antibodies 17-1A and BR 55-2 Against the Colorectal Carcinoma Cell Line HT29," Cancer Immun Immunothe 46, pp. 213-220.
Cha et al, "Human Interferon Regulatory Factor 2 Gene," *The Journal of Biological Chemistry*, vol. 269, No. 7, Feb. 18, 1994, pp. 5279-5287.
Goto et al. "A Novel Membrane Antigen Selectively Expressed on Terminally Differentiated Human B Cells" Blood, vol. 84, No. 5, Sep. 1999, pp. 1922-1930.
Ishikawa et al. "Molecular Cloning and Chromosomal Mapping of a Bone Marrow Stromal Cell Surface Gene, BST2, That May Be Involved in Pre-B-Cell Growth" A Stromal Cell Molecule Involved in Pre-B-Cell Growth, Cenomics 26, pp. 527-534, 1996.

(Continued)

Primary Examiner — Christine J Saoud
Assistant Examiner — Jegatheesan Seharaseyon
(74) Attorney, Agent, or Firm — Morrison & Foerster LLP

(57) ABSTRACT

An enhancer of expression, in the myeloma cell, of HM1.24 antigen, said enhancer comprising interferon-α or interferon-γ, or IRF-2 protein as an active ingredient. Interferon-α or interferon-γ is expected to enhance the expression of HM1.24 antigen by activating the promoter of a gene encoding HM1.24 antigen.

7 Claims, 9 Drawing Sheets

OTHER PUBLICATIONS

Kosaka et al. "Advances in Biology and Pathogenesis of Multiple Myeloma" Japanese Clinical vol. 53, No. 3, Mar. 1995, pp. 627-635.

Langer et al. "Interferon Receptors" Immunology Today, vol. 9, No. 12, 1988, pp. 393-400.

Lengyel "Tumor-suppressor Genes: News About the Interferon Connection" Proc. Natl. Acad. Sci. USA, vol. 90, pp. 5893-5895, Jul. 1993.

Ludwig et al. "Current Controversies in Cancer—Should Alpha-interferon be Included as Standard Treatment in Multiple Myeloma?" European Journal of Cancer, vol. 34, No. 11, pp. 12-24, 1998.

Mellstedt et al. (Oct. 1991) "Treatment of Multiple Myeloma with Interferon Alpha: the Scandinavian Experience," Br J Haernatol vol. 79, Supp 1, pp. 21-25.

Office Action Report from European Patent Office dated Apr. 6, 2004.

Ozaki et al. (1997) "Immunotherapy of Multiple Myeloma with a Monoclonal Antibody Directed Against a Plasma Cell-Specific Antigen, HM1.24" *Blood* 90(8), pp. 3179-3186.

Ozaki, S. et al., "Humanized Anti-HM1.24 Antibody Mediates Myeloma Cell Cytotoxicity That Is Enhanced By Cytokine Stimulation of Effector Cells" full text. *Blood* (Jun. 1999) vol. 93. No. 11, P3922-30.

Ozaki, S. et al., "Interferon-Alpha and -Gamma Enhance The HM1.24 Expression On Myeloma Cells Through The STAT-Signaling Pathway," *Blood* (Nov. 15, 1999) vol. 94, No. 10 Suppl.1 Part 1, p. 549a.

Pestka et al. "Interferons and Their Actions" Am. Rev. Biochem. vol. 56, 1987, pp. 727-777.

Platanias, Leonidas C. et al. "Signaling Pathways Activated by Interferons," Experimental Hematology 27 (1999), pp. 1583-1592.

*The Merck Index* ($12^{th}$ Ed.) Merck & Co., Inc., 1996, pp. 856-857, entries 5016 and 5018.

Ohtomo, Toshihiko et al., "Molecular Cloning and Characterization of a Surface Antigen Preferentially Overexpressed on Multiple Myeloma Cells", Biochemical and Biophysical Research Communications 258 (1999) pp. 583-591.

Verharr, Marlies et al., "In Vitro Upregulation Of Carcinoembryonic Antigen Expression by Combinations Of Cytokines" Cancer Lett., (May 1999), vol. 139, No. 1., pp. 67-73.

Wiklund et al. (1991) "Recombinant Interferon-γ Inhibits the Growth of IL-6 Dependent Human Multiple Myeloma Cell Lines in Vitro," Eur J Haematol vol. 46, pp. 231-239.

European Office Action mailed Oct. 21, 2005, directed to EP Application No. 00953561.8.

Aman, P. et al. (1990). "An Epstein-Barr virus immortalization associated gene segment interferes specifically with the IFN-Induced anti-proliferative response in human B-lymphoid cell lines." *The EMBO Journal.* 9(1):147-152.

Berzoksky, J. et al. (1993) "Immunogenicity and Antigen Structure," Chapter 8 in Fundamental Immunology. William E. Paul, ed. Raven Press, Ltd. NY, NY. p. 242.

Billard, C. et al. (Mar. 1986) "Treatment of Hairy Cell Leukemia With Recombinant Alpha Interferon: II. In Vivo Down-Regulation of Alpha Interferon Receptors on Tumor Cells." *Blood*. 67(3):821-826.

Blasius, A. et al., (2006). "Bone Marrow Stromal Cell Antigen 2 Is A Specific Marker of Type I IFN-Producing Cells in the Naïve Mouse, but a Promiscous Cell Surface Antigen following IFN Stimulation." J. lmmunol. 177:3260-3265.

Darnell, J. Jr. et al. (Jun. 3, 1994). "Jak-STAT Pathways and Transcriptional Activation in Response to IFNs and Other Extracellular Signaling Proteins." *Science*.264:1415-1421.

Dron, M. et al. (1993). "Interferon-Resistant Daudi Cells are Deficient in Interferon-α-Induced ISGF3α Activation, but Remain Sensitive to the Interferon-α-Induced Increase in ISGF3γ Content." *Journal of Interferon Research*. 13:377-383.

Inaba, K. et al. (Apr. 1986) "Contrasting Effect of α/β- and γ-lnterferons on Expression of Macrophage la Antigens," J. Exp. Med.163:1030-1035.

Kanda, K. et al. (Nov. 1992). "The EBNA2-Related Resistance Towards Alpha Interferon (IFN-α) in Burkitt's Lymphoma Cells Effects Induction of IFN-Induced Genes but Not the Activation of Transcription Factor ISGF-3." *Molecular and Cellular Biology.* 12(11):4930-4936.

Koenig, S. et al., (2000)."Cloning of an Interferon Regulatory Factor 2 Isoform With Different Regulatory Ability," *Nucleic Acids Research*.28(21):4219-4224.

Maio, M. et al. (Jun. 1, 1989)."Modulation by Interferons of HLA Antigen, High-Molecular-Weight Melanoma-associated Antigen, and Intercellular Adhesion Molecule 1 Expression by Cultured Melanoma Cells with Different Metastatic Potential," Cancer Research 49:2980-2987.

Pfeffer, L. et al. (May 1, 1990). "The Down-Regulation of α-Interferon. Receptors in Human Lymphoblastoid Cells: Relation to Cellular Responsiveness to the Antiproliferative Action of α-Interferon." *Cancer Research.* 50:2654-2657.

Sequence search alignment for SEQ ID No:2 for U.S. Appl. No. 10/467,358; 2 pages.

Supplementary Partial Search Report dated Oct. 26, 2005, directed to foreign application 02711350.5; 4 pages.

Tanaka, N. et al. (Aug. 1993). "Recognition DNA Sequences of Interferon Regulatory Factor 1 (IRF-1) and IRF-2, Regulators of Cell Growth and the Interferon System," *Molecular and Cellular Biology*. 13(8):4531-4538.

Wasserman, W. et al. (Apr. 2004). "Applied Bioinformatics for the Identification of Regulatory Elements." *Nature Reviews/Genetics*. 5:276-287.

Beckman, R., et al., (2007) "Antibody constructs in cancer therapy" *Cancer* vol. 109(2): 170-179.

Cespedes, M., et al. (2006) "Mouse models in oncogenesis and cancer therapy" *Clin Transl Oncol* vol. 8(5):3318-329.

Dennis, Carina (2006) "Off by a whisker" *Nature* vol. 442:739-741.

Fujimori, K., et al., (1990) "A modeling analysis of monoclonal antibody percolation through tumors: A binding-site barrier" *J. Nucl. Med.* vol. 31:1191-1198.

Kosaka, M. et al. US Office Action directed towards U.S. Appl. No. 10/467,358, mailed Jan. 5, 2010; 20 pages.

Rudnick, S., et al., (2009) "Affinity and avidity in antibody-based tumor targeting" *Cancer Biotherapy and Radiopharmaceuticals* vol. 24(2):155-162.

Talmadge, J., et al. (2007) "Murine models to evaluate novel and conventional therapeutic strategies for cancer" *The American Journal of Pathology* vol. 170(3): 793-804.

Thurber, G., et al., (2008) "Antibody tumor penetration: Transport opposed by systemic and antigen-mediated clearance" *Advanced Drug Delivery Reviews* vol. 60:1421-1434.

Voskoglou-Nomikos, T., et al. (2003) "Clinical predictive value of the in Vitro cell line, human xenograft, and mouse allograft preclinical cancer models" *Clinical Cancer Research* vol. 9:4227-4239.

Muralikrishna, K. et al., (1997) "Differential modulation of LAK and ADCC functions of natural killer cells from AK-5 tumor-bearing rats by IL-2, IL-12 and IFN-γ" *Cytokine, Cellular & Molecular Therapy* vol. 3:51-58.

Sung, M. et al., (1996) "Protective effects of interferon-γ on squamous-cell carcinoma of head and neck targets in antibody-dependent cellular cytotoxicity mediated by human natural killer cells" *Int. J. Cancer* vol. 66:393-399.

Kosaka, M. et al. US Office Action directed towards U.S. Appl. No. 10/467,358, mailed Apr. 19, 2010; 12 pages.

Kosaka, Masaaki et al. (1995). "Advances in Biology and Pathogenesis of Multiple Myeloma," *Nippon Rinsho Japanese Journal of Clinical Medicine* 53(3):627-635. With translation of summary.

Ozaki, Shuji et al. (1999). "Humanized Anti-HM1.24 Antibody Mediates Myeloma Cell Cytotoxicity That is Enhanced by Cytokine Stimulation of Effector Cells,"*Blood* 93(11):3922-3930.

Tokyo Kagaku Dojin Co., Ltd.(1990). Interferon "Cytokine", *Toshiaki Osawa etd.*:115-135.

Hashimoto-Gotoh, Tamotsu et al. (1995). "An Oligodeoxyribonucleotide-directed dual amber method for site-directed Mutagenesis," *Gene*152:271-275.

Zoller, Mark J. et al.(1983). "Oligonucleotide-Directed Mutagenesis of DNA Fragments Cloned into M13 Vectors," *Methods in Enzymology* 100:468-500.

Kramer, Wilfried et al. (1984). "The Gapped Duplex DNA Approach to Oligonucleotide-directed Mutation Construction,"*Nucleic Acids Research* 12(24):9441-9456.

Kunkel, Thomas A. (1985). "Rapid and Efficient Site-specific Mutagenesis without Phenotypic Selection," *Proc. Natl. Acad. Sci. USA.* 82:488-492.

New Cell Engineering Experimental Protocol edited by Dept. of Oncology, Inst. of Medical Science, Univ. Of Tokyo (1993). pp. 241-248.

Mark, D.F. et al. (1984). "Site-specific Mutagenesis of the Human Fibroblast Interferon Gene," *Proc. Natl. Acad. Sci. USA.* 81:5662-5666.

Itoh, Susuma et al. (1989). "Sequence of a cDNA coding for Human IRF-2," *Nucleic Acids Research* 17(20):8372.

Harada, Hisashi et al. (1989). "Structurally similar but Functionally Distinct Factors, IRF-1 and IRF-2, Bind to the Same Regulatory Elements of IFN and IFN-Inducible Genes," *Cell* 58:729-739.

Goto, T. et al. (1991). "Establishment of Myeloma Cell Line (KPC-32) and Production of Monoclonal Antibody that Recognizes Cell Surface Antigen," *Japan J. Clin. Hematol.* 32:758.

Kearney, John F. et al. (1979). "A new Mouse Myeloma Cell Line that has Lost Immunoglobulin Expression but Permits the Construction of Antibody-Secreting Hybrid Cell Lines," *The Journal of Immunology* 123(4):1548-1550.

Yelton, D.E. (1978). "Fusion of Mouse Myeloma and Spleen Cells," *Current Topics in Microbiology and Immunology* 81:7 pages.

Kohler, G. et al. (1976). "Derivation of Specific Antibody-producing Tissue Culture and Tumor Lines by Cell Fusion," *Eur. J. Immunol.* 6:511-519.

Margulies, David H. (1976). "Somatic Cell Hybridization of Mouse Myeloma Cells," *Cell* 8:405-415.

Shulman, M. et al. (1978). "A Better Cell Line for Making Hybridomas Secreting Specific Antibodies," *Nature* 276:269-270.

De St. Groth, S.F. et al. (1980). "Production of Monoclonal Antibodies: Strategy and Tactics," *Journal of Immunological Methods* 35:1-21.

Trowbridge, Ian S. (1978). "Interspecies Spleen-Myeloma Hybrid Producing Monoclonal Antibodies Against Mouse Lymphocyte Surface Glycoprotein, T200," *J. Exp. Med.* 148:313-323.

Galfre, G. et al. (1979). "Rat x Rat Hybrid Myelomas and a Monoclonal Anti-Fd Portion of Mouse IgG," *Nature* 277:131-133.

Galfre, G. et al. (1981). "Preparation of Monoclonal Antibodies: Strategies and Procedures," *Methods in Enzymology* 73:3-46.

Chirgwin, J.M. et al. (1979). "Isolation of Biologically Active Ribonucleic Acid from Sources Enriched in Ribonuclease," *Biochemistry* 18:5294-5299.

Chomczynski, P. et al. (1987). "Single-Step Method of RNA Isolation by Acid Guanidinium Thiocyanate-Phenol-Chloroform Extraction," *Analytical Biochemistry* 162(24):156-159.

Frohman, Michael A. et al. (1988). "Rapid Production of Full-Length cDNAs from Rare Transcripts: Amplification Using a Single Gene-Specific Oligonucleotide Primer," *Proc. Natl. Acad. Sci. USA*, 85: 8998-9002.

Belyavsky, A. et al. (1989). "PCR-based cDNA Library Construction: General cDNA Libraries at the Level of a few Cells," *Nucleic Acids Research* 17(8):2919-2932.

Sato, K. et al. (1993). "Reshaping a Human Antibody to Inhibit the Interleukin 6-Dependent Tumor Cell Growth," *Cancer Research* 53:851-856.

Mulligan, Richard C. (1979). "Synthesis of Rabbit β-globin in Cultured Monkey Kidney Cells Following infection with a SV40 β-globin Recombinant Genome," Nature 277:108-114.

Mizushima, S. et al. (1990). "pEF-BOS, a Powerful Mammalian Expression Vector," *Nucleic Acids Research* 18 (17):5322.

Ward, E.S. et al. (1989). "Binding Activities of a Repertoire of Single Immunoglobulin Variable Domains Secreted from *Escherichia coli*" *Nature* 341: 544-546.

Ward, E.S. (1992). "Antibody Engineering: the Use of *Escherichia coli* as an Expression Host,"*Faseb J.* 6:2422-2427.

Better, M. et al. (1988). "*Escherichia coli* Secretion of an Active Chimeric Antibody Fragment," *Science* 240:1041-1043.

Lei, S. P. et al. (1987). "Characterization of the Erwinia Carotovora pelB Gene and its Product Pectate Lyase," *Journal of Bacteriology*, 169: 4379-4383.

Ebert, K. M. (1994). "Induction of Human Tissue Plasminogen Activator in the Mammary Gland of Transgenic Goats," *Bio/Technology* 12:699-702.

Maeda, S. et al. (1985). "Production of Human α-interferon in Silkworm using a Baculovirus Vector," *Nature* 315(9):592-594.

Ma, J. K.-C. et al. (1994). "Assembly of Monoclonal Antibodies with IgG1 and IgA Heavy Chain Domains in Transgenic Tobacco Plants," *Eur. J. Immunol.* 24:131-138.

Smith, R.I.F. et al. (1994). "Recombinant Polymeric IgG: An Approach to Engineering More Potent Antibodies," *Bio/Technology* 12:683-688.

Smith, R.I.F et al. (1995). "Addition of a µ-Tailpiece to IgG Results in Polymeric Antibodies with Enhanced Effector Functions Including Complement-Mediated Cytolysis by IgG4," *The Journal of Immunology* 154:2226-2236.

Shuford, W. et al. (1991). "Effect of Light Chain V Region Duplication on IgG Oligomerization and in Vivo Efficacy," *Science* 252:724-727.

Caron, P.C. et al. (1992). "Engineered Humanized Dimeric Forms of IgG Are More Effective Antibodies," *J. Exp. Med.* 176:1191-1195.

Shopes, B. (1992). "A Genetically Engineered Human IgG Mutant with Enhanced Cytolytic Activity," *The Journal of Immunology* 148(9):2918-2922.

Wolff, E.A. (1993). "Monoclonal Antibody Homodimers: Enhanced Antitumor Activity in Nude Mice," *Cancer Research* 53:2560-2565.

Norderhaug, L. et al. (1991). "Chimeric Mouse Human IgG3 Antibodies with an IgG4-like Hinge Region Induce Complement-mediated Lysis more Efficiently than IgG3 with Normal Hinge," *Eur. J. Immunol.* 21:2379-2384.

Clark, (1993) "Protein Engineering of Antibody Molecules for Prophylactic and Therapeutic Applications in Man", pp. 1; cover page.

Eisenthal et al. (1989) "Systemic induction of Cells Mediating Antibody-dependent Cellular Cytotoxicity Following Administration of interleukin 2", *Cancer Research*, Dec. 15, 1989, vol. 49, pp. 6953-6959.

Evans et al., (Jul. 10, 1997) "IL-15 Mediates Anti-Tumor Effects After Cyclophosphamide injection of Tumor-bearing Mice and Enhances Adoptive Immunotherapy: The Potential Role of NK Cell Subpopulations." *Cellular Immunology*, 179:66-73 (Abstract only).

Gill et al., (Oct. 1, 1989) "Synergistic Antitumor Effects of Interleukin 2 and the Monoclonal Lym-1 Against Human Burkitt Lymphoma Cells in Vitro and in Vivo," *Cancer Research* 49:5377-5379.

Hanton et al. (1984) The Reaction of Antibody-Dependent Cell Mediated Cytotoxicity (ADCC), "*Annales de Recherches Veterinaires*" 15(4):443-454. (English translation of Abstract).

Hird et al. (1990) "Immunotheraphy with Monoclonal Antibodies." *Genes and Cancer*, (Monograph). 183-189 and cover page.

Kay, Neil K. (1987) "Restoration of Impaired Natural Killer Cell Activity of B-Chronic Lymphocytic Leukemia Patients by Recombinant Interleukin-2", *American Journal of Hematology*: 24(2):161-167.

Kosaka et al., U.S. Office Action mailed Feb. 24, 2006, directed towards U.S. Appl. No. 10/428,085; 10 pages.

Kosaka et al., U.S. Office Action mailed Nov. 21, 2006, directed towards U.S. Appl. No. 10/428,085; 11 pages.

Kosaka et al., U.S. Office Action mailed Sep. 6, 2007, directed towards U.S. Appl. No. 10/428,085; 8 pages.

Kosaka et al., U.S. Office Action mailed Jun. 11, 2008, directed towards U.S. Appl. No. 10/428,085; 7 pages.

Kosaka et al., U.S. Office Action mailed Mar. 5, 2009, directed towards U.S. Appl. No. 10/428,085; 4 pages.

Mihich et al. (1986) "Future Perspectives for Biological Response Modifiers: A View Point." *Seminars in Oncology*. 13(2):234-254.

Ottonello et al. (Jun. 15, 1996) "Monoclonal Lym-1 Antibody-Dependent Lysis of B-Lymphoblastoid Tumor Targets by Human Complement and Cytokine-Exposed Monocuclear and Neutrophilic Polymorphonuclear Luekocytes." *Blood*. 87(12):5171-5178.

Ozaki et al. (1996) "Localization and Imaging of Human Plasmacytoma Xenografts in Severe Combined Immunodeficiency Mice by a New Murine Monoclonal Antibody, Anti-HM1.24." *Tokushima J. Exp. Med.* 43:7-15.

Parkinson, David R. (Dec. 29, 1995) "Present Status of Biological Response Modifiers in Cancer", *American Journal of Medicine*, 99(6A):54S-56S.

Pawelec et al. (1989) "Partial Correction of Defective Generation of Lymphokine-Activated Killer Cells in Patients with Chronic Myelogenous Leukemia After in vivo Treatment with Interferon-α (Wellferon)", *Cancer Immunology Immunotherapy*. 29(1):63-66.

Peest et al. (1995) "Low Dose Recombinant Interleukin-2 Therapy in Advanced Multiple Myeloma", *British Journal of Haematology*. 89(2):328-337.

Schlom, J. (1991) "Monoclonal Antibodies; They're More and Less Than You Think", *Molecular Foundations of Oncology*. 95-134 and cover page.

Stewart et al. (1997) "Immunogene Therapy with interleukin 12 (IL-12), B7-1 and Flt3 Ligand (Flt3L) in a Murine Myeloma Model: IL-12 and B7-1 Expressing Cells Confer Protective Immunity", *Blood*, vol. 90(10) Suppl1, Part 1: 358A-359A.

Takeuchi et al. (Dec. 1996) "Induction by Interleukin-15 of Human Killer Cell Activity Against Lung Cancer Cell Lines and Its Regulatory Mechanisms." *Japanese Journal of Cancer Research*. 87(12):1251-1258 (Abstract only).

Vachino et al. (Nov. 15, 1991) "Complement Activaion in Cancer Patients Undergoing Immunotherapy With Interleukin-2 (IL-2): Binding of Complement and C-Reactive Protein by IL-2-Activated Lymphocytes", *Blood*, 78(10):2505-2513.

Kosaka et al., U.S. Office Action mailed Dec. 20, 2011, directed to related U.S. Appl. No. 13/085,741; 19 pages.

Aman, P. et al, (1990), "An Epstein-Barr virus immortalization associated gene segment interferes specifically with the IFN-Induced anti-proliferative response in human B-lymphoid cell lines," *The EMBO Journal*, 9(1):147-152.

"ATCC: Cell Biology Collection" located at http:www.atcc.org/common/catalog/numSearch/numResults.cfm?atccNum=CRL-1621 retrieved on Oct. 18, 2007; 3 pages.

Berzoksky, J. et al. (1993) "Immunogenicity and Antigen Structure," Chapter 8 in Fundamental Immunology, William E. Paul, ed. Raven Press, Ltd. NY, NY. p. 242.

Billard, C. et al, (Mar. 1986) "Treatment of Hairy Cell Leukemia With Rocombinant Alpha Interferon: II, In Vivo Down-Regulation of Alpha Interferon Receptors on Tumor Cells," *Blood*. 67(3):821-826.

Blasius, A. et al., (2006), "Bone Marrow Stromal Cell Antigen 2 is A Specfic Marker of Type I IFN-Producing Cells in the Naïve Mouse, but a Promiscous Cell Surface Antigen following IFN Stimulation," J. Immunol. 177:3260-3265.

Darnell, J. Jr., et al. (Jun. 3, 1994), "Jak-STAT Pathways and Transcriptional Activation in Response to IFNs and Other Extracellular Signaling Proteins." *Science*.264:1415-1421.

Dovhey, S. et al. "Loss of Interferon-γ Inducibility of TAP1 and LMP2 in a Renal Cell Carcinoma Cell Line," Cancer Research 60, Oct. 15, 2000, pp. 5789-5796.

Dron, M. et al. (1993), "Interferon-Resistant Daudi Cells are Deficient in Inteferon-α-Induced ISGF3α Activation, but Remain Sensitive to the Interferon-α-Induced Increase in ISGF3γ Content." *Journal of Interferon Research*, 13:377-383.

Inaba, K. et al, (Apr. 1986) "Contrasting Effect of α/β- and γ-Interferons on Expression of Macrophage la Antigens," J. Exp. Med. 163:1030-1035.

International Search Report mailed on Nov. 21, 2000, directed to International Patent Application No. PCT/JP00/05617; 4 pages.

International Search Report mailed on May 21, 2002, directed to International Patent Application No. PCT/JP02/00989; 8 pages.

Jesse, T. et al., (1998). "Interferon Regulatory Factor-2 is A Transcriptional Activator in Muscle Where it Regulates Expression of Vascular Cell Adhesion Molecule-1," *The Journal of Cell Biology*, 140(5):1265-1276.

Kanda, K. et al. (Nov. 1992). "The EBNA2-Related Resistance Towards Alpha Interferon (IFN-α) in Burkitt's Lymphoma Cells Effects Induction of IFN-Induced Genes but Not the Activation of Transcription Factor ISGF-3." *Molecular and Cellular Biology*. 12(11):4930-4936.

Koenig, S. et al., (2000). "Cloning of an Interferon Regulatory Factor 2 Isoform With Different Regulatory Ability," *Nucleic Acids Research*.28(21):4219-4224.

Kosaka, M. et al., US Office Action directed towards U.S. Appl. No. 10/069,290 mailed Feb. 4, 2005; 10 pages.

Kosaka, M. et al., US Office Action directed towards U.S. Appl. No. 10/069,290 mailed Oct. 14, 2005; 7 pages.

Kosaka, M. et al. US Office Action directed towards U.S. Appl. No. 10/467,358 mailed Sep. 28, 2006; 16 pages.

Kosaka, M. et al. US Office Action directed towards U.S. Appl. No. 10/467,358 mailed Mar. 28, 2007; 15 pages.

Kosaka, M. et al. US Office Action directed towards U.S. Appl. No. 10/467,358 mailed Nov. 7, 2007; 14 pages.

Kosaka, M. et al. US Office Action directed towards U.S. Appl. No. 10/467,358 mailed Jun. 30, 2008; 16 pages.

Kosaka, M. et al. US Office Action directed towards U.S. Appl. No. 10/467,358 mailed Mar. 11, 2009; 20 pages.

Maio, M. et al. (Jun. 1, 1989). "Modulation by Interferons of HLA Antigen, High-Molecular-Weight Melanoma-associated Antigen, and Intercellular Adhesion Molecule 1 Expression by Cultured Melanoma Cells with Different Metastatic Potential," Cancer Research 49:2980-2987.

Pfeffer, L. et al. (May 1, 1990). "The Down-Regulation of α-Interferon Receptors in Human Lymphoblastoid Cells: Relation to Cellular Responsiveness to the Antiproliferative Action of α-interferon." *Cancer Research*. 50:2654-2657.

Search output from ATCC website for anti-HM1.24 monoclonal antibody/ hybridoma deposit; retrieved on Sep. 25, 2006; 2 pages.

Sequence search alignment for SEQ ID No. 2 for U.S. Appl. No. 10/467,358; 2 pages, (2007).

Stedman Definition of "myeloma" Stedmans' On-line Medical Dictionary, 27th Ed., retrieved on Mar. 9, 2009; 3 pages.

Supplementary Partial Search Report dated Oct. 26, 2005, directed to foreign application 02711350.5: 4 pages.

Tanaka, N. et al. (Aug. 1993), "Recognition DNA Sequences of Interferon Regulatory Factor 1 (IRF-1) and IRF-2, Regulators of Cell Growth and the Interferon System," *Molecular and Cellular Biology*. 13(8):4531-4538.

TFSEARCH Search Result; retrieved on Aug. 20, 2009; 1 page.

Wasserman, W. et al. (Apr. 2004). "Applied Bioinformatics for the Identification of Regulatory Elements." *Nature Reviews/Genetics*. 5:276-287.

Xu, B. et al. (Sep. 15, 1994). "Primary Leukemia Cells Resistant to α-Interferon in Vitro are Defective in the Activation of the DNA-Binding Factor Interferon-Stimulated Gene Factor 3." *Blood*. 84(6):1942-1949.

METHOD FOR TREATING MYELOMA UTILIZING AN EXPRESSION ENHANCER FOR HM1.24 ANTIGEN

CROSS-REFERENCE TO RELATED APPLICATION

This application is a continuation of Ser. No. 10/069,290, filed Feb. 25, 2002, now abandoned, which is a 371 of PCT/JP2000/05617, filed Aug. 22, 2000, the disclosure of which is hereby incorporated by reference.

FIELD OF THE INVENTION

The present invention relates to the use of interferon-α, interferon-γ, and IRF-2 protein as an expression enhancer for HM1.24 antigen in myeloma.

BACKGROUND ART

Myeloma, also termed as plasmacytoma and multiple myeloma, is a neoplastic disease characterized by the accumulation of monoclonal plasma cells in the bone marrow. Myeloma is a disease in which terminally differentiated B cells or plasma cells that produce and secrete immunoglobulins are monoclonally increased predominantly in the bone marrow, and thereby monoclonal immunoglobulins or their constituent light chains or heavy chains are detected in the blood of patients with this disease.

For the treatment of myeloma, chemotherapeutic agents have so far been used, but no effective therapeutic agents have been discovered that lead to complete remission of the disease and that prolong the survival period of patients with myeloma, and thereby the appearance of drugs that have therapeutic effects of myeloma have long been sought after.

On the other hand, Goto, T. et al. have reported a monoclonal antibody (mouse anti-HM1.24 antibody) that was obtained by immunizing mice with human myeloma cells (Blood (1994) 84, 1922-1930). When anti-HM1.24 antibody was administered to a mouse transplanted with human myeloma cells, the antibody accumulated in tumor tissues in a specific manner (Masaaki Kosaka et al., Nippon Rinsho (Japan Clinical) (1995) 53, 627-635), suggesting that anti-HM1.24 antibody could be applied in the diagnosis of tumor localization by radioisotopic labeling, missile therapies such as radiotherapy, and the like.

In the above Blood (1994) 84, 1922-1930, it has been described that anti-HM1.24 antibody has an in vitro cytotoxic activity on a human myeloma cell line RPMI8226. It has also been shown that chimeric anti-HM1.24 antibody that is mouse anti-HM1.24 antibody turned chimeric, and a humanized reshaped anti-HM1.24 antibody specifically bind to myeloma cells and have a cytotoxic activity (Blood (1999) 93, 3922-3920).

Thus, HM1.24 antigen has been highly expressed specifically on myeloma cells that are terminally differentiated B cells and, as the anti-HM1.24 antibody that recognizes this antigen exhibits a cell-killing activity in proportion to the number of HM1.24 molecules on the cell surface, an immunotherapy employing anti-HM1.24 antibody is thought to be an effective method of treating multiple myeloma. Thus, if the amount expressed of HM1.24 antigen, an antigen of anti-HM1.24 antibody, on the cell surface could be enhanced, the administration of a smaller amount of the antibody is expected to provide an equal cytotoxic activity thereby lowering side effects.

On the other hand, interferon was discovered to be a substance that exhibits a suppressing activity of viral growth and is known to be classified into four groups of α, β, γ, and ω and to have a variety of biological activities (Pestka, S., et al., Ann. Rev. Biochem. (1987) 56, 727-777; Langer, J. A., et al., Immunology Today (1988) 9, 393-400). However, there were no reports on the fact that interferon-α and interferon-γ had an effect of increasing the amount expressed of HM1.24 antigen in myeloma cells.

On the other hand, interferon regulatory factor (IRF)-1 and -2 were identified as transcription regulatory factors of the IFN-β gene. IRF-1 and -2 are known to bind to the same gene regulatory sequence: IRF-1 and IRF-2 act in an antagonistic manner in that IRF-1 acts as a transcription activation factor, whereas IRF-2 acts as a transcription suppressing factor. The NIH3T3 cells in which IRF-2 was highly expressed have been demonstrated to exhibit enhanced cell saturation density, colony formation in the methylcellulose gel, and a tumorigenic property in nude mice, and IRF-2 acts as an oncogene.

On the other hand, recent advances in research have indicated that IRF-2 is required for the expression of histone H4 that acts to control the cell cycle. IRF-2 is also shown to increase the expression of vascular cell adhesion molecule-1 (VCAM-1) in muscle cells, and it is becoming increasingly clear that the acid region (182 to 218) is involved in the activation of VCAM-1. Based on this, it is known that IRF-2 not only acts as a transcription regulatory factor but as a transcription activation factor.

However, it was not known that IRF-2 protein binds to the promoter (HM1.24 promoter) of the HM1.24 antigen gene, and activates said promoter.

DISCLOSURE OF THE INVENTION

Current methods of treating myeloma are, as mentioned above, not satisfactory yet and, accordingly, the appearance of epoch-making therapeutic drugs or methods that prolong the patient's survival are awaited. The treatment of myeloma with anti-HM1.24 antibody is likely to be an epoch-making therapeutic treatment and thus there is a need for methods of exhibiting the effect of anti-HM1.24 antibody more efficiently.

Thus, it is an object of the present invention to provide means to enhance the myeloma-suppressing effect of anti-HM1.24 antibody by increasing the amount expressed of HM1.24 antigen in myeloma cells.

In order to provide such methods, the inventors of the present invention have carried out a search for drugs that enhance the expressed amount of HM1.24 antigen, and as a result, have found that interferon-α and interferon-γ have the desired effects, and thereby have completed the present invention.

Thus, the present invention provides an enhancer of expression in the myeloma cell of a protein (HM1.24 antigen) having the amino acid sequence as set forth in SEQ ID NO: 2, said enhancer comprising interferon-α or interferon-γ as an active ingredient.

The present invention also provides a therapeutic agent for myeloma, said agent comprising, as an active ingredient, an antibody that specifically binds to:

(1) interferon-α or interferon-γ, and (2) a protein having the amino acid sequence as set forth in SEQ ID NO: 2, and that has a cytotoxic activity.

Typical of the above myeloma is multiple myeloma.

Said antibody is preferably a monoclonal antibody, a chimeric antibody or a humanized antibody, and preferably has a cytotoxic activity.

The inventors of the present invention have carried out a search for activating agents of the HM1.24 promoter, and have found that IRF-2 protein has the desired activity, and thereby have completed the present invention.

Thus, the present invention provides an enhancer of expression in the myeloma cell of a protein (HM1.24 antigen) having the amino acid sequence as set forth in SEQ ID NO: 2, said enhancer comprising IRF-2 protein as an active ingredient.

The present invention also provides an activating agent of the HM1.24 promoter, said agent comprising IRF-2 protein as an active ingredient.

The present invention also provides a therapeutic agent for myeloma comprising, as an active ingredient, an antibody that specifically binds to:

(1) IRF-2 protein, and
(2) a protein having the amino acid sequence as set forth in SEQ ID NO: 2, and that has a cytotoxic activity.

Typical of the above myeloma is multiple myeloma.

Said antibody is preferably a monoclonal antibody, a chimeric antibody or a humanized antibody, and preferably has a cytotoxic activity.

The present invention also provides an enhancer of expression in the myeloma cell of HM1.24 antigen, said enhancer comprising, as an active ingredient, a compound that enhances the expression of IRF-2 protein.

The present invention also provides an activating agent of the HM1.24 promoter, said agent comprising a compound that enhances the expression of IRF-2 protein.

The present invention also provides a method of screening agents that enhance the expression of HM1.24 antigen.

The present invention also provides a kit comprising:

(1) an antibody that specifically binds to a protein having the amino acid sequence as set forth in SEQ ID NO: 2, and that has a cytotoxic activity; and
(2) an instruction manual that directs the administration to the patient of the above antibody in combination with a pharmaceutical agent that enhances the expression of a protein having the amino acid sequence as set forth in SEQ ID NO: 2.

Said myeloma is for example multiple myeloma. Said antibody is preferably humanized anti-HM1.24 antibody. The pharmaceutical agent that enhances the expression of a protein having the amino acid sequence as set forth in SEQ ID NO: 2 is preferably interferon-α or interferon-γ.

The present invention provides a pharmaceutical composition for the treatment of a patient with myeloma comprising an antibody that specifically binds to a protein having the amino acid sequence as set forth in SEQ ID NO: 2 and that has a cytotoxic activity, wherein said composition is administered to the patient in combination with a pharmaceutical agent that enhances the expression of a protein having the amino acid sequence as set forth in SEQ ID NO: 2.

Said myeloma is for example multiple myeloma. Said antibody is preferably humanized anti-HM1.24 antibody. The pharmaceutical agent that enhances the expression of a protein having the amino acid sequence as set forth in SEQ ID NO: 2 is preferably interferon-α or interferon-γ.

EMBODIMENT FOR CARRYING OUT THE INVENTION

Interferon-α and Interferon-γ

Figure 1:
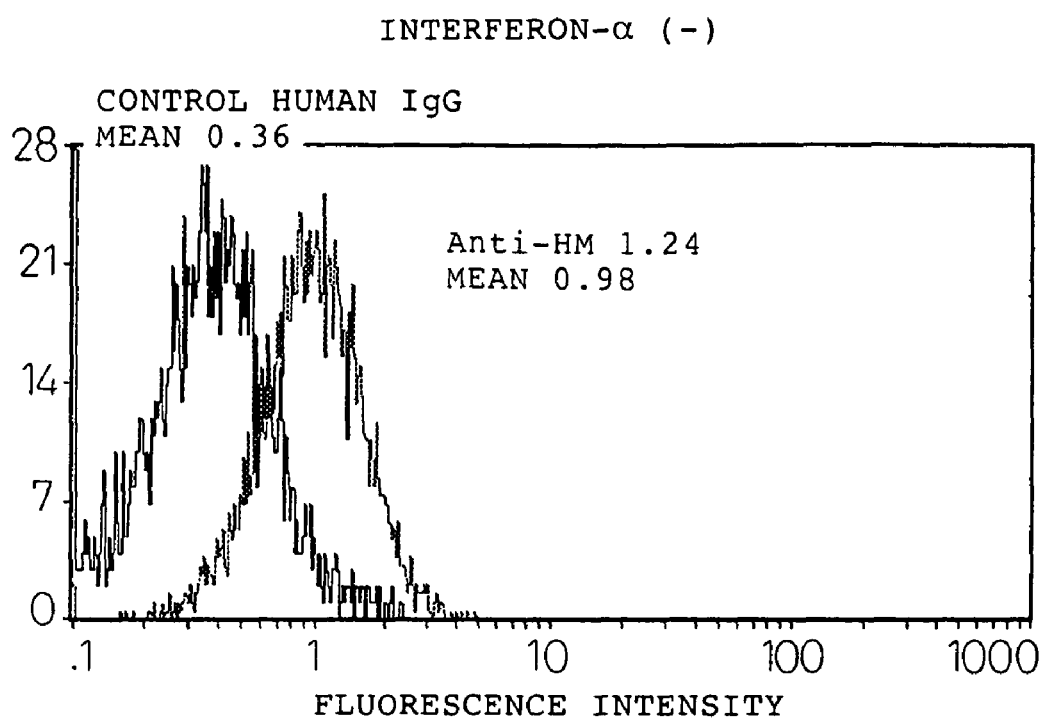
FIG. 1 shows the result of an experiment in which a myeloma cell line U266 cultured in the absence (upper) or presence (bottom) of interferon-α was analyzed by flow cytometry using human IgG (control) or anti-HM1.24 antibody as a label.
Figure 1:
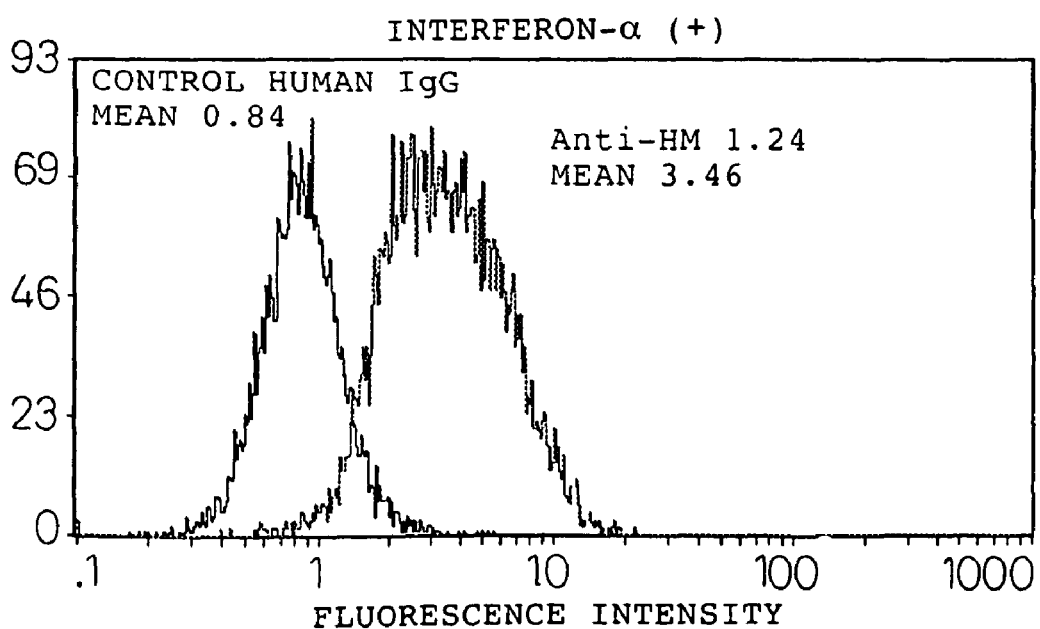

Interferon-α and interferon-γ for use in the present invention may be mutants as long as they have an activity of increasing the amount expressed of HM1.24 antigen. In order to determine the amount expressed of HM1.24 antigen, as described in Examples, myeloma cells are harvested from a myeloma cell line or a patient with myeloma and then subjected to flow cytometry for detection. As mutants, they may be interferon-α and interferon-γ in which one or several, or a plurality, of amino acid residues have been deleted, substituted, or inserted or added.

As methods of introducing deletion, substitution, or insertion, there can be used site-directed mutagenesis that alters the corresponding gene (Hashimoto-Gotoh, Gene (1005) 152, 271-275, Zoller, Methods Enzymol. (1983) 100, 468-500, Kramer, Nucleic Acids Res. (1984) 12, 9441-8456, Kunkel, Proc. Natl. Acad. Sci. USA (1985) 82, 489-492, "New Cell Engineering Experimental Protocolw edited by Dept. of Oncology, Inst. of Medical Science, Univ. of Tokyo (1993) pp. 241-248).

It is also possible to use "Site-Directed Mutagenesis System" (GIBCO-BRL) and "Quickchange Site-Directed Mutagenesis Kit" (Stratagene) employing commercially available PCR. Amino acid mutations in proteins may sometimes take place in nature. That such a protein, in which mutation has been introduced, has an activity equal to the original protein has been shown in Mark, Proc. Natl. Acad. Sci. USA (1984) 81, 5662-5666.

In the substitution of amino acid residues, it is preferred to substitute between amino acids whose properties are conserved. For example, substitution is preferred between hydrophobic amino acids (A, I, L, M, F, P, W, Y, V), hydrophilic amino acids (R, D, N, C, E, Q, G, H, K, S, T), amino acids having aliphatic side chains (G, A, V, L, I, P), amino acids having hydroxyl group-containing side chains (S, T, Y), amino acids having sulfur-containing side chains (C, M), amino acids having carboxylic acid- and amide-containing side chains (D, N, E, Q), amino acids having base-containing side chains (R, K, H), and amino acids having aromatic group-containing side chains (H, F, Y, W).

Furthermore, as mutants, peptide fragments of interferon-α or interferon-γ may be used. In particular, peptide fragments that have binding sites with interferon-α or interferon-γ receptors. Preferably they are peptides comprised of 100 or more, more preferably 130 or more, still more preferably 150, and most preferably 160 or more contiguous amino acid residues.

IRF-2 Protein

Interferon regulatory factor (IRF)-1 and -2 were identified as a transcription regulatory factor of the IFN-β gene. IRF-1 and -2 are known to bind to the same gene regulatory sequence: IRF-1 and IRF-2 act in an antagonistic manner in that IRF-1 acts as a transcription activation factor, whereas IRF-2 acts as a transcription suppressing factor. The NIH3T3 cells in which IRF-2 is highly expressed has been demonstrated to exhibit enhanced cell saturation density, colony formation in the methylcellulose gel, and a tumorigenic property in nude mice, and IRF-2 acts as an oncogene.

On the other hand, recent advances in research have indicated that IRF-2 is required for the expression of histone H4 that acts for the control of cell cycle. IRF-2 is also shown to increase the expression of vascular cell adhesion molecule-1 (VCAM-1) in muscle cells, and it is becoming increasingly clear that the acid region (182 to 218) is involved in the activation of VCAM-1. Based on this, it is known that IRF-2 not only acts as a transcription regulatory factor but as a transcription activation factor.

Hybridoma

The hybridoma produced by the antibody for use in the present invention can be basically constructed using a known technology as described below. Thus, HM1.24 antigen protein or a HM1.24 antigen-expressing cell IL-6 may be used as a sensitizing antigen and is immunized in the conventional method of immunization. The immune cells thus obtained are fused with known parent cells in the conventional cell fusion process, and then monoclonal antibody-producing cells are screened by the conventional screening method to construct the desired hybridoma.

Specifically, monoclonal antibody may be obtained in the following manner. For example, as the HM1.24 antigen-expressing cell which is the sensitizing antigen to obtain the antibody, a human multiple myeloma cell line KPMM2 (Japanese Unexamined Patent Publication (Kokai) No. 7-236475) and KPC-32 (Goto, T. et al., Jpn. J. Clin. Hematol. (1991) 32, 1400) can be used. As the sensitizing antigen, it is also possible to use a protein having the amino acid sequence as set forth in SEQ ID NO: 1 or a peptide or a polypeptide containing an epitope recognized by anti-HM1.24 antibody.

The cDNA of the protein having the amino acid sequence as set forth in SEQ ID NO 1 used as the sensitizing antigen is inserted into the XbaI cleavage site of the pUC19 vector to prepare a plasmid pRS38-pUC19. *E. coli* having the plasmid pRS38-pUC19 has been internationally deposited under the provisions of the Budapest Treaty as *Escherichia coli* DH5α (pRS38-pUC19) on Oct. 5, 1993 with the National Institute of Bioscience and Human Technology, Agency of Industrial Science and Technology, of 1-3, Higashi 1-chome, Tsukuba city, Ibaraki Pref., Japan, as FERM BP-4434 (Japanese Unexamined Patent publication (Kokai) No. 7-196694). Using the cDNA fragment contained in this plasmid pRS38-pUC19, a peptide or a polypeptide that contains an epitope recognized by anti-HM1.24 antibody can be constructed by a gene engineering technology.

Mammals to be immunized with the sensitizing antigen are not specifically limited, and they are preferably selected in consideration of their compatibility with the parent cell for use in cell fusion. They generally include rodents such as mice, rats, and hamsters.

Immunization of animals with a sensitizing antigen is carried out using a known method. A general method, for example, involves the intraperitoneal or subcutaneous administration of a sensitizing antigen to the mammal.

Specifically, a sensitizing antigen which has been diluted and suspended in an appropriate amount of phosphate buffered saline (PBS) or physiological saline etc. is mixed, as desired, with an appropriate amount of a common adjuvant, for example Freund's complete adjuvant. After being emulsified, it is preferably administered to the mammal for several times every 4 to 21 days. Alternatively, a suitable carrier may be used at the time of immunization of the sensitizing antigen.

After immunizing in this manner and confirming the increase in the desired antibody levels in the serum, immune cells are harvested from the mammal and are subjected to cell fusion.

The mammalian myeloma cells as the other parent cells which are subjected to cell fusion with the above-mentioned immune cells preferably include various known cell lines such as P3X63Ag8.653 (J. Immunol. (1979) 123:1548-1550), P3X63Ag8U.1 (Current Topics in Microbiology and Immunology (1978) 81: 1-7), NS-1 (Kohler, G. and Milstein, C., Eur. J. Immunol. (1976) 6: 511-519), MPC-11 (Margulies, D. H. et al., Cell (1976) 8: 405-415), SP2/0 (Shulman, M. et al., Nature (1978) 276: 269-270), FO (de St. Groth, S. F. et al. J. Immunol. Methods (1980) 35: 1-21), S194 (Trowbridge, I. S., J. Exp. Med. (1978) 148: 313-323), R210 (Galfre, G. et al., Nature (1979) 277: 131-133) and the like.

Cell fusion between the above immune cells and the myeloma cells may be essentially conducted in accordance with a known method such as is described in Milstein et al. (Kohler, G. and Milstein, C., Methods Enzymol. (1981)73: 3-46) and the like.

More specifically, the above cell fusion is carried out in the conventional nutrient broth in the presence of, for example, a cell fusion accelerator. As the cell fusion accelerator, for example, polyethylene glycol (PEG), Sendai virus (HVJ) and the like may be used, and, in addition, an adjuvant such as dimethyl sulfoxide etc. may be added as desired to enhance the efficiency of the fusion.

The preferred ratio of the immune cells and the myeloma cells to be used is, for example, 1 to 10 times more immune cells than the myeloma cells. Examples of culture media to be used for the above cell fusion include RPMI1640 medium and MEM culture medium suitable for the growth of the above myeloma cell lines, and the conventional culture medium used for this type of cell culture. A serum supplement such as fetal calf serum (FCS) may be added.

In cell fusion, predetermined amounts of the above immune cells and the myeloma cells are mixed well in the above culture liquid, to which a PEG solution previously heated to about 37° C., for example a PEG solution with a mean molecular weight of about 1000 to 6000, is added at a concentration of 30 to 60% (w/v), and mixed to obtain the desired fusion cells (hybridomas). Then by repeating the sequential addition of a suitable culture liquid and centrifugation to remove the supernatant, cell fusion agents etc. which are undesirable for the growth of the hybridoma can be removed.

Said hybridoma is selected by culturing in a conventional selection medium, for example, the HAT culture medium (a culture liquid containing hypoxanthine, aminopterin, and thymidine). Culturing in said HAT culture medium is continued generally for a period of time sufficient to effect killing of the cells (non-fusion cells) other than the desired hybridoma, generally several days to several weeks. Then, the conventional limiting dilution method is conducted in which the hybridomas that produce the desired antibody are screened and cloned.

In addition to obtaining the above hybridoma by immunizing an animal other than the human with an antigen, it is also possible to sensitize human lymphocytes in vitro with HM1.24 antigen or HM1.24 antigen-expressing cells, and to allow the resulting sensitized lymphocytes to be fused with a human-derived myeloma cell, for example U266, and thereby to obtain the desired human antibody having the activity of binding HM1.24 antigen or HM1.24 antigen-expressing cells (see Japanese Examined Patent Publication (Kokoku) No. 1-59878). Furthermore, a transgenic animal having a repertoire of human antibody genes is immunized with HM1.24 antigen or HM1.24 antigen-expressing cells to obtain the desired antibody according to the above-mentioned method (see International Patent Application WO 93/12227, WO 92/03918, WO 94/02602, WO 94/25585, WO 96/34096, and WO 96/33735).

The monoclonal antibody-producing hybridomas thus constructed can be subcultured in the conventional culture liquid, or can be stored for a prolonged period of time in liquid nitrogen.

In order to obtain monoclonal antibodies from said hybridoma, there may be employed a method in which said hybridoma is cultured in the conventional method and the antibodies are obtained as the culture supernatant, or a method in which the hybridoma is administered to and grown in a mammal compatible with said hybridoma and the antibodies are obtained as the ascites, or other methods. The former method is suitable for obtaining high-purity antibodies, whereas the latter is suitable for a large scale production of antibodies.

Monoclonal Antibody

Specifically the anti-HM1.24 antibody-producing hybridoma can be constructed using the method of Goto, T. et al. (Blood (1994) 84: 1922-1930). It can be conducted by: a method in which the anti-HM1.24 antibody-producing hybridoma that was internationally deposited under the provisions of the Budapest Treaty as FERM BP-5233 on Apr. 27, 1995 with the National Institute of Bioscience and Human Technology, Agency of Industrial Science and Technology, of 1-3, Higashi 1-chome, Tsukuba city, Ibaraki Pref., Japan, is intraperitoneally injected to BALB/c mice (manufactured by CLEA Japan) to obtain the ascites, from which the anti-HM1.24 antibody is purified, or: a method in which said hybridoma is cultured in a suitable culture medium such as the RPMI1640 medium containing 10% bovine fetal serum and 5% BM-Condimed H1 (manufactured by Boehringer Mannheim), the hybridoma SFM medium (manufactured by GIBCO-BRL), the PFHM-II medium (manufactured by GIBCO-BRL) and the like, and the anti-HM1.24 antibody can be purified from the supernatant.

Recombinant Antibody

A recombinant antibody which was produced by the recombinant gene technology in which an antibody gene was cloned from the hybridoma and integrated into a suitable vector which was then introduced into a host can be used in the present invention as monoclonal antibody (see, for example, Carl, A. K., Borrebaeck, and James, W. Larrick, THERAPEUTIC MONOCLONAL ANTIBODIES, published in the United Kingdom by MACMILLAN PUBLISHERS LTD. 1990).

Specifically, mRNA encoding the variable region (V) of the desired antibody is isolated from the hybridoma producing the antibody. The isolation of mRNA is conducted by preparing total RNA using, for example, a known method such as the guanidine ultracentrifuge method (Chirgwin, J.M. et al., Biochemistry (1979) 18, 5294-5299), the AGPC method (Chmczynski, P. et al., (1987) 162, 156-159), and then mRNA is purified from the total RNA using the mRNA Purification kit (manufactured by Pharmacia) and the like. Alternatively, mRNA can be directly prepared using the QUICKPREP mRNA Purification Kit (manufactured by Pharmacia).

cDNA of the V region of the antibody may be synthesized from the mRNA thus obtained using a reverse transcriptase. cDNA may be synthesized using the AMV Reverse Transcriptase First-strand cDNA Synthesis Kit and the like. Alternatively, for the synthesis and amplification of cDNA, the 5'-Ampli FINDER RACE Kit (manufactured by Clontech) and the 5'-RACE method (Frohman, M. A. et al., Proc. Natl. Acad. Sci. U.S.A. 1988) 85, 8998-9002; Belyavsky, A. et al., Nucleic Acids Res. (1989) 17, 2919-2932) that employs PCR may be used. The desired DNA fragment is purified from the PCR product obtained and may be ligated to vector DNA. Moreover, a recombinant vector is constructed therefrom and then is introduced into *E. coli* etc., from which colonies are selected to prepare the desired recombinant vector. The base sequence of the desired DNA may be confirmed by a known method such as the dideoxy method.

Once the DNA encoding the V region of the desired antibody has been obtained, it may be ligated to DNA encoding the constant region (C region) of the desired antibody, which is then integrated into an expression vector. Alternatively, the DNA encoding the V region of the antibody may be integrated into an expression vector which already contains DNA encoding the C region of the antibody.

In order to produce the antibody for use in the present invention, the antibody gene is integrated as described below into an expression vector so as to be expressed under the control of the expression regulatory region, for example an enhancer and/or a promoter. Subsequently, the expression vector may be transformed into a host cell and the antibody can then be expressed therein.

Altered Antibody

In accordance with the present invention, artificially altered recombinant antibody such as chimeric antibody and humanized antibody can be used for the purpose of lowering heterologous antigenicity against humans. These altered antibody can be produced using known methods.

Chimeric antibody can be obtained by ligating the thus obtained DNA encoding the V region of antibody to DNA encoding the C region of human antibody, which is then integrated into an expression vector and introduced into a host for production of the antibody therein (see European Patent Application EP 125023, and International Patent Application WO 96/02576). Using this known method, chimeric antibody useful for the present invention can be obtained.

For example, *E. coli* having the plasmid that contains the L chain and the H chain of chimeric anti-HM1.24 antibody has been internationally deposited under the provisions of the Budapest Treaty as *Escherichia coli* DH5α (pUC19-1.24L-gκ) and *Escherichia coli* DH5α (pUC19-1.24H-gγ1), respectively, on Aug. 29, 1996 with the National Institute of Bioscience and Human Technology, Agency of Industrial Science and Technology, of 1-3, Higashi 1-chome, Tsukuba city, Ibaraki Pref., Japan, as FERM BP-5646 and FERM BP-5644, respectively (see Japanese Patent Application No. 8-264756).

Humanized antibody which is also called reshaped human antibody has been made by transplanting the complementarity determining region (CDR) of antibody of a mammal other than the human, for example mouse antibody, into the CDR of human antibody. The general recombinant DNA technology for preparation of such antibodies is also known (see European Patent Application EP 125023 and International Patent Application WO 96/02576).

Specifically, a DNA sequence which was designed to ligate the CDR of mouse antibody with the framework region (FR) of human antibody is synthesized by the PCR method from several divided oligonucleotides having sections overlapping with one another at the ends thereof. The DNA thus obtained is ligated to the DNA encoding the C region of human antibody and then is integrated into an expression vector, which is introduced into a host for antibody production (see European Patent Application EP 239400 and International Patent Application WO 96/02576).

For the FR of human antibody ligated through CDR, the complementarity determining region that forms a favorable antigen binding site is selected. When desired, amino acids in the framework region of the antibody variable region may be substituted so that the complementarity determining region of reshaped human antibody may form an appropriate antigen biding site (Sato, K. et al., Cancer Res. (1993) 53, 851-856).

For example, *E. coli* having the plasmid that contains the L chain and the H chain of humanized anti-HM1.24 antibody has been internationally deposited under the provisions of the Budapest Treaty as *Escherichia coli* DH5α (pUC19-RVLa-AHM-gκ) and *Escherichia coli* DH5α (pUC19-RVHr-AHM-gγ1), respectively, on Aug. 29, 1996 with the National Institute of Bioscience and Human Technology, Agency of Industrial Science and Technology, of 1-3, Higashi 1-chome, Tsukuba city, Ibaraki Pref., Japan, as FERM BP-5645 and FERM BP-5643, respectively (International Patent Application WO 98-14580).

For chimeric antibody or humanized antibody, the C region of human antibody is used, and as the C region of human antibody that exhibits cytotoxic activity, human Cγ, for example Cγ1, Cγ2, Cγ3, and Cγ4 can be used. Among them, antibody having Cγ1 and Cγ3 in particular has potent cytotoxic activity, i.e. ADCC activity and CDC activity, and is used preferably in the present invention.

Chimeric antibody consists of the variable region of antibody derived from a mammal other than the human and the C region derived from human antibody, whereas humanized antibody consists of the complementarity determining region of antibody derived from a mammal other than the human and the framework region (FR) and the C region of antibody derived from human antibody. Accordingly, antigenicity thereof in the human body has been reduced so that they are useful as the active ingredient of the therapeutic agents of the present invention.

A preferred embodiment of the humanized antibody for use in the present invention includes humanized anti-HM1.24 antibody (see Japanese Patent Application No. 8-264756).

Expression and Production

Antibody genes constructed as described above may be expressed and obtained in a known method. In the case of mammalian cells, expression may be accomplished using an expression vector containing a commonly used useful promoter, the antibody gene to be expressed, and DNA in which the poly A signal has been operably linked at 3' downstream thereof or a vector containing said DNA. Examples of the promoter/enhancer include human cytomegalovirus immediate early promoter/enhancer.

Additionally, as a promoter/enhancer which can be used for the expression of antibody for use in the present invention, there can be used viral promoters/enhancers such as retrovirus, polyoma virus, adenovirus, and simian virus 40 (SV40), and promoters/enhancers derived from mammalian cells such as human elongation factor 1α (HEF1α).

For example, expression may be readily accomplished by the method of Mulligan et al. (Nature (1979) 277, 108) when SV40 promoter/enhancer is used, or by the method of Mizushima et al. (Nucleic Acids Res. (1990) 18, 5322) when HEF1α promoter/enhancer is used.

In the case of *E. coli*, expression may be conducted by operably linking a commonly used useful promoter, a signal sequence for antibody secretion, and the antibody gene to be expressed, followed by expression thereof. As the promoter, for example, there can be mentioned lacZ promoter and araB promoter. The method of Ward et al. (Nature (1098) 341, 544-546; FASEB J. (1992) 6, 2422-2427) may be used when lacZ promoter is used, and the method of Better et al. (Science (1988) 240, 1041-1043) may be used when araB promoter is used.

As a signal sequence for antibody secretion, when produced in the periplasm of *E. coli*, the pe1B signal sequence (Lei, S. P. et al., J. Bacteriol. (1987) 169, 4379) can be used. After separating the antibody produced in the periplasm, the structure of the antibody is appropriately refolded before use (see, for example, WO 96/30394).

As an origin of replication, there can be used those derived from SV40, polyoma virus, adenovirus, bovine papilloma virus (BPV) and the like. Furthermore, for the amplification of the gene copy number in the host cell system, expression vectors can include as selectable markers the aminoglycoside transferase (APH) gene, the thymidine kinase (TK) gene, *E. coli* xanthine guaninephosphoribosyl transferase (Ecogpt) gene, the dihydrofolate reductase (dhfr) gene and the like.

For the production of antibody for use in the present invention, any production system can be used. The production system of antibody preparation comprises the in vitro and the in vivo production system. As the in vitro production system, there can be mentioned a production system which employs eukaryotic cells and the production system which employs prokaryotic cells.

When the eukaryotic cells are used, there are the production systems which employ animal cells, plant cells, and fungal cells. Known animal cells include (1) mammalian cells such as CHO cells, COS cells, myeloma cells, baby hamster kidney (BHK) cells, HeLa cells, and Vero cells, (2) amphibian cells such as *Xenopus oocytes*, or (3) insect cells such as sf9, sf21, and Tn5. Known plant cells include, for example, those derived from the genus *Nicotiana*, more specifically cells derived from *Nicotiana tabacum*, which is subjected to callus culture. Known fungal cells include yeasts such as the genus *Saccharomyces*, more specifically *Saccharomiyces cereviceae*, or filamentous fungi such as the genus *Aspergillus*, more specifically *Aspergillus niger*.

When the prokaryotic cells are used, there are the production systems which employ bacterial cells. Known bacterial cells include *Escherichia coli* (*E. coli*), and *Bacillus subtilis*.

By introducing, via transformation, the gene of the desired antibody into these cells and culturing the transformed cells in vitro, the antibody can be obtained. Culturing is conducted in the known methods. For example, as the culture liquid, DMEM, MEM, RPMI1640, and IMDM can be used, and serum supplements such as fetal calf serum (FCS) may be used in combination. In addition, antibodies may be produced in vivo by implanting cells into which the antibody gene has been introduced into the abdominal cavity of an animal and the like.

As further in vivo production systems, there can be mentioned those which employ animals and those which employ plants. When animals are used, there are the production systems which employ mammals and insects.

As mammals, goats, pigs, sheep, mice, and cattle can be used (Vicki Glaser, SPECTRUM Biotechnology Applications, 1993). Also as insects, silkworms can be used.

When plants are used, tobacco, for example, can be used.

Antibody genes are introduced into these animals or plants, and the antibodies are produced in such animals or plants, and recovered therefrom. For example, an antibody gene is inserted into the middle of the gene encoding protein which is inherently produced in the milk such as goat β casein to prepare fusion genes. DNA fragments containing the fusion gene into which the antibody gene has been inserted are injected into a goat embryo, and the embryo is introduced into a female goat. The desired antibody is obtained from the milk produced by the transgenic goat borne to the goat who received the embryo or offsprings thereof. In order to increase the amount of milk containing the desired antibody produced by the transgenic goat, hormones may be given to the transgenic goat as appropriate. (Ebert, K. M. et al., Bio/Technology (1994) 12, 699-702).

When silkworms are used, baculovirus into which the desired antibody gene has been inserted is infected to the silkworm, and the desired antibody can be obtained from the body fluid of the silkworm (Susumu, M. et al., Nature (1985) 315, 592-594). Moreover, when tobacco is used, the desired antibody gene is inserted into an expression vector for plants, for example pMON 530, and then the vector is introduced into a bacterium such as *Agrobacterium tumefaciens*. The bacterium is then infected to tobacco such as *Nicotiana tabacum* to obtain the desired antibody from the leaves of the tobacco (Julian, K.-C. Ma et al., Eur. J. Immunol. (1994) 24, 131-138).

When antibody is produced in the in vitro or in vivo production systems, as described above, DNA encoding the heavy chain (H chain) or the light chain (L chain) of antibody may be separately integrated into an expression vector and the hosts are transformed simultaneously, or DNA encoding the H chain and the L chain may be integrated into a single expression vector and the host is transformed therewith (see International Patent Application WO 94-11523).

The antibody produced as described above can be bound to various molecules such as polyethylene glycol (PEG) for use as a modified antibody. "Antibody" as used herein includes these modified antibodies. In order to obtain these modified antibody, the antibody obtained may be chemically modified. These methods have already been established in the field of the art.

Separation and Purification of Antibody

Antibodies produced and expressed, as described above can be separated from the inside or outside of the cell or from the host and then may be purified to homogeneity. Separation and purification of the antibody for use in the present invention may be accomplished by affinity chromatography. As the column used for such affinity chromatography, there can be mentioned Protein A column and Protein G column. Examples of the column employing Protein A column are Hyper D, POROS, Sepharose F. F. and the like.

Alternatively, methods for separation and purification conventionally used for proteins can be used without any limitation. Separation and purification of the antibody for use in the present invention may be accomplished by combining, as appropriate, chromatography other than the above-mentioned affinity chromatography, filtration, ultrafiltration, salting-out, dialysis and the like. Chromatography includes, for example, ion exchange chromatography, hydrophobic chromatography, gel-filtration and the like.

Determination of Antibody Concentration

The concentration of antibody obtained in the above method can be determined by the measurement of absorbance or by ELISA and the like. Thus, when absorbance measurement is employed, the antibody for use in the present invention or a sample containing the antibody is appropriately diluted with PBS(−) and then the absorbance is measured at 280 nm, followed by calculation using the absorption coefficient of 1.35 OD at 1 mg/ml. When the ELISA method is used, measurement is conducted as follows. Thus, 100 µl of goat anti-human IgG (manufactured by BIO SOURCE) diluted to 1 µg/ml in 0.1 M bicarbonate buffer, pH 9.6, is added to a 96-well plate (manufactured by Nunc), and is incubated overnight at 4° C. to immobilize the antibody.

After blocking, 100 ml each of appropriately diluted antibody of the present invention or a sample containing the antibody, or 100 ml of human IgG (manufactured by CAPPEL) as the standard is added, and incubated at room temperature for 1 hour. After washing, 100 µl of 5000-fold diluted alkaline phosphatase-labeled anti-human IgG antibody (manufactured by BIO SOURCE) is added, and incubated at room temperature for 1 hour. After washing, the substrate solution is added and incubated, followed by the measurement of absorbance at 405 nm using the MICROPLATE READER Model 3550 (manufactured by Bio-Rad) to calculate the concentration of the desired antibody.

FCM Analysis

Reactivity of the antibody of the present invention with lymphocytes may be examined by flow cytometry (FCM) analysis. As the cells, established cell lines or freshly isolated cells can be used. As established cell lines, there may be used myeloma-derived RPMI8226 (ATCC CCL 155), myeloma-derived U266 (ATCC TIB 196), myeloma-derived KPMM2, myeloma-derived KPC-32, and plasmacytoma-derived ARH-77 (ATCC CRL 1621), and the like.

After washing the above cells in PBS(−), 100 µl of antibody or a control antibody diluted to 25 µg/ml in the FACS buffer (PBS(−) containing 2% bovine fetal serum and 0.05% sodium azide) is added thereto, which is then incubated on ice for 30 minutes. After washing with the FACS buffer, 100 µl of 25 µg/ml FITC-labeled goat anti-mouse antibody (GAM, manufactured by Becton Dickinson) is added thereto, which is then incubated on ice for 30 minutes. After washing with the FACS buffer, the cells are suspended in 600 µl or 1 ml of the FACS buffer, and each cell may be measured for its fluorescence intensity using the FACScan (manufactured by Becton Dickinson).

Screening Method

In order to screen the expression enhancer of HM1.24 antigen, for example, the cells that have not been stimulated and that are not expressing HM1.24 antigen or the cells that at least are expressing the antigen are determined using FCM analysis. For example, the cells described in Examples and a test substance are incubated for 1-2 days, and then stained with mouse anti-human HM1.24 antibody as a primary antibody. The cells are washed and further stained with FITC-labeled anti-mouse IgG antibody as a secondary antibody. Finally, after washing the cells, the fluorescence intensity of FITC is measured by flow cytometry.

Furthermore, instead of the above indirect staining, FCM analysis by direct staining may be used in which the cells are treated with a high concentration of immunoglobulin, and then stained, after blocking Fc receptors, with FITC-labeled anti-human HM1.24 antibody.

It is also possible to screen the expression enhancers of HM1.24 antigen using a reporter gene assay and using the HM1.24 promoter sequence. As the reporter gene, luciferase can be used. A plasmid is constructed that contains the HM1.24 promoter sequence upstream of the reporter gene, after which it is transformed into the cells, and the cells obtained are cultured with a test substance for 1-2 days, and the cells recovered are subjected to luciferase assay to screen drugs that enhance the expression of HM1.24 antigen.

Cytotoxic Activity

Measurement of ADCC Activity

The antibody for use in the present invention is one which has, for example, an ADCC activity as the cytotoxic activity.

According to the present invention, the ADCC activity on myeloma cells can be measured in the following manner. First, mononuclear cells are isolated as the effector cells from human peripheral blood or bone marrow by the gravity centrifuge method.

As the target cells (Target cell: T), RPMI8226 (ATCC CCL 155), U266 (ATCC TIB 196), KPMM2, KPC-32, ARH-77 (ATCC CRL 1621) or the like are labeled with $^{51}$Cr to be prepared as the target cells. Subsequently, to the labeled target cells is added the antibody to be measured for the ADCC activity and incubated. Effector cells at a suitable ratio to the target cells are then added and incubated.

After the incubation, the supernatant is removed and measured for radioactivity using a gamma counter, whereupon 1% NP-40 can be used for measurement of the maximum free radioactivity. The cytotoxic activity (%) can be calculated as $(A-C)/(B-C)\times 100$, in which A is radioactivity (cpm) liberated in the presence of the antibody, B is radioactivity (cpm) liberated by NP-40, and C is radioactivity (cpm) liberated by the medium alone containing no antibody.

Enhancement of Cytotoxic Activity

In order to exhibit cytotoxic activity such as an ADCC activity, it is preferred to use Cγ, in particular Cγ1 and Cγ3 as the constant region (C region) of antibody in humans. Furthermore, a more potent ADCC activity or CDC activity can be induced by adding, altering, or modifying part of the amino acids in the C region of antibody.

By way of example, there can be mentioned the construction of an IgM-like polymer of IgG by amino acid substitution (Smith, R. I. F. & Morrison, S. L. BIO/TECHNOLOGY (1994) 12, 683-688), the construction of an IgM-like polymer of IgG by amino acid addition (Smith, R. I. F. et al., J. Immunology (1995) 154, 2226-2236), the expression of a tandemly-ligated gene encoding L chain (Shuford, W. et al., Science (1991) 252, 724-727), the dimerization of IgG by amino acid substitution (Caron, P. C. et al., J. Exp. Med. (1992) 176, 1191-1195, Shopes, B., J. Immunology (1992) 148, 2918-2922), the dimerization of IgG by chemical modification (Wolff, E. A. et al., Cancer Res. (1993) 53, 2560-2565), and the introduction of the effector function by altering an amino acid(s) in the hinge region of antibody (Norderhaug, L. et al., Eur. J. Immunol. (1991) 21, 2379-2384) and the like.

These can be accomplished by means of the oligomer site-specific mutagenesis using a primer, the addition of a base sequence using a restriction enzyme cleavage site, and the use of a chemical modifier that creates a covalent bond.

Treatment of Patients

One embodiment of the present invention concerns a method of treating myeloma, preferably multiple myeloma, by administering to the patient a pharmaceutical agent that enhances the amount expressed of HM1.24 antigen and anti-HM1.24 antibody. The pharmaceutical agent that enhances the amount expressed of HM1.24 antigen is preferably interferon-α or interferon-γ. Interferon and anti-HM1.24 antibody may be administered together or separately. In the latter case, preferably interferon is given first, followed by the administration of anti-HM1.24 antibody within 96 hours. The interval between the interferon administration and the anti-HM1.24 antibody administration is not limited as long as the amount expressed of HM1.24 antigen is being enhanced by the administration of interferon, but it is preferably within 96 hours, more preferably 72 hours, still more preferably 48 hours. Alternate administration of interferon and anti-HM1.24 antibody a plurality of times depending on the clinical response of the patient is within the scope of the present invention. The route of administration is preferably directly into the blood circulation, and intravenous administration or intraarterial administration is preferred. Continued administration is possible and an intravenous drip may be used.

Another embodiment of the present invention concerns a therapeutic agent for myeloma comprising interferon-α or interferon-γ and anti-HM1.24 antibody. The therapeutic agent of the present invention may contain a harmaceutically acceptable vehicle that has been used for interferon and antibody preparations, such as physiological saline or 5% dextran, together with a common stabilizer or an excipient.

Another embodiment of the present invention provides a kit for treating a patient with myeloma, wherein kit comprises a pharmaceutical composition comprising anti-HM1.24 antibody as an active ingredient and an instruction manual that contains description on combined therapy with interferon-α or interferon-γ.

Another embodiment of the present invention provides a pharmaceutical composition comprising anti-HM1.24 antibody as an active ingredient for treating a patient with myeloma, wherein said composition is used in combination with interferon-α or interferon-γ.

EXAMPLES

Example 1

Enhancement of the Amount Expressed of HM1.24 Antigen in Myeloma Cells by Interferon-α

A human myeloma cell line U266 (ATCC TIB 196) and myeloma cells derived from the bone marrow of a patient with multiple myeloma were cultured in a RPMI1640 medium (Sigma, St Louis, Mo., USA) containing 10% fetal bovine serum (Whittaker Bioproducts, Inc., Walkersville, Md., USA) in a 5% carbon dioxide incubator at 37° C. The hybridoma that produces mouse anti-HM1.24 antibody has been internationally deposited as FERM BP-5233 (deposition date: Apr. 27, 1995) with the National Institute of Bioscience and Human Technology, Agency of Industrial Science and Technology, of 1-3, Higashi 1-chome, Tsukuba city, Ibaraki Pref.

Myeloma cells ($1\times10^5$/ml) were cultured in the presence or absence of 1000 U/ml of the natural type interferon-α (Otsuka Pharmaceutical, Tokyo) for 48 hours, and changes in HM1.24 antigen (the base sequence encoding this is shown in SEQ ID NO: 1) were determined by flow cytometry. After the cells were washed with phosphate buffer (Gibco BRL, Grand Island, N.Y., USA) supplemented with 0.1% bovine serum albumin (Sigma, St Louis, Mo., USA) and 0.02% sodium azide, they were suspended into PBS (100 μl) supplemented with human immunoglobulin (3 mg/ml, Green Cross, Osaka), and were allowed to react at 4° C. for 15 minutes.

Thereafter, 2 μl of FITC-human IgGl (1 mg/ml) or FITC-anti-HM1.24 antibody (1 mg/ml) was added to stain at 4° C. for 60 minutes. When the patient's myeloma cells were used, 20 μl of PE-anti-CD38 (Becton Dickinson, San Jose, Calif., USA) was added for double staining to identify the myeloma cell. After staining, the cells were washed twice with PBS, and were stored in PBS containing 1% paraformaldehyde (Wako Pure Chemical Industries, Ltd., Osaka). Subsequently, the expression of HM1.24 antigen was analyzed using a flow cytometer (EPICS XL, Coulter, Hialeah, Fla., USA).

Figure 2:
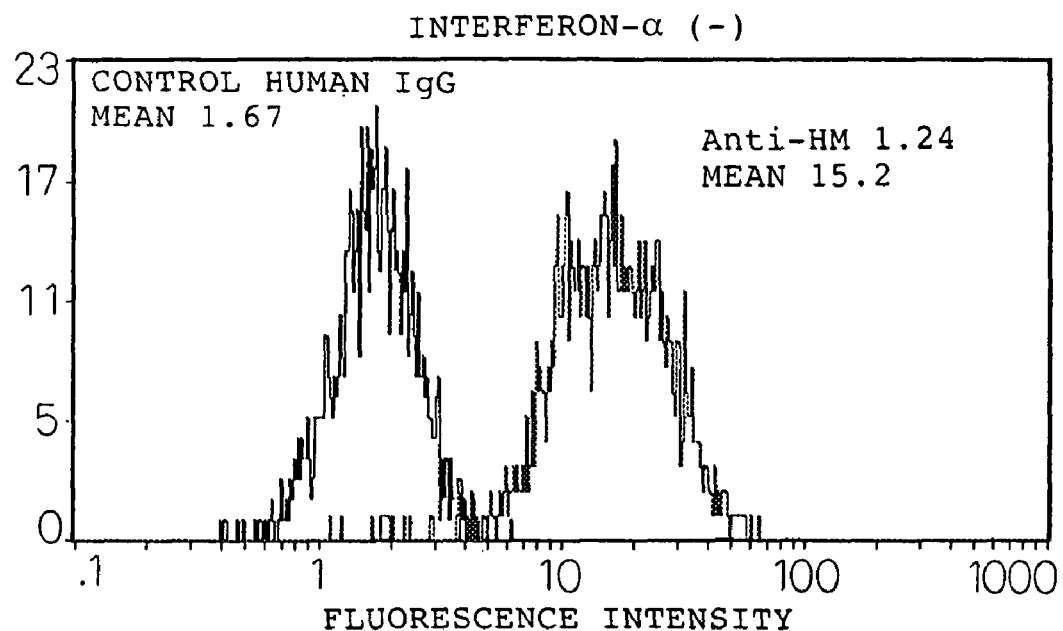
FIG. 2 shows the result of an experiment in which the myeloma cells of the patient cultured in the absence (upper) or presence (bottom) of interferon-α was analyzed by flow cytometry using human IgG (control) or anti-HM1.24 antibody as a label.
Figure 2:
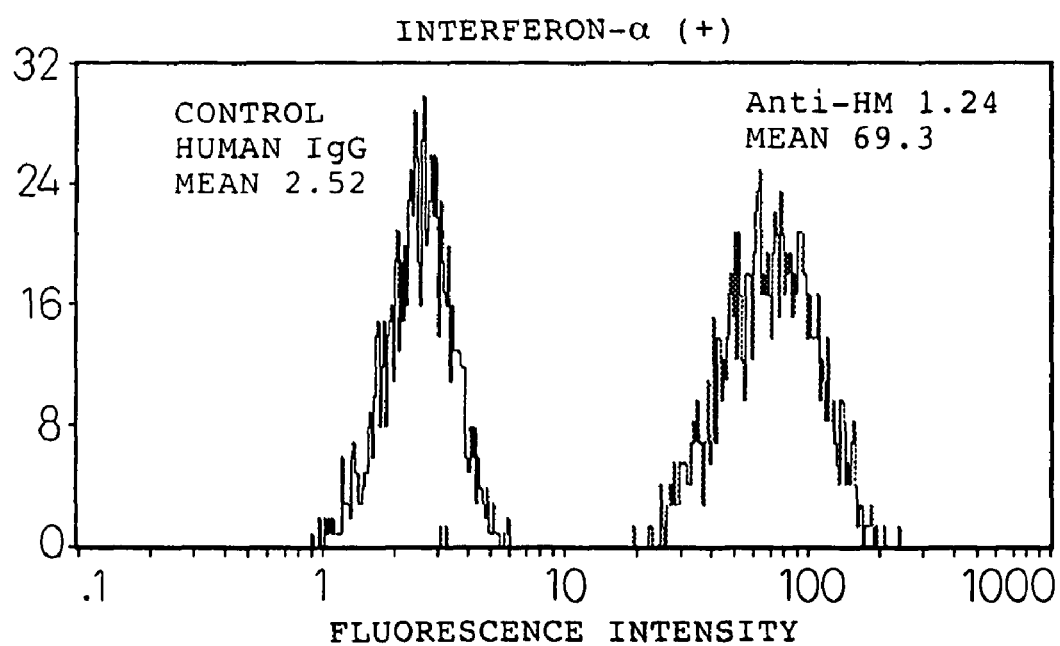

As a result, a myeloma cell line U266 (FIG. 1) and the patient's myeloma cells (FIG. 2) were expressing HM1.24 antigen at a condition of no stimulation, and the stimulation with interferon-α further increased the amount expressed of HM1.24 antigen.

Interferon-α further enhanced the expression of HM1.24 antigen in the myeloma cell, and increased the number of anti-HM1.24 antibodies that bind to the myeloma cell. Since the therapeutic anti-tumor effect by anti-HM1.24 antibody is proportional to the number of binding antibodies, treatment with anti-HM1.24 antibody after the amplified of interferon-α is expected to become a therapy that enhances the therapeutic effect by antibody and further enhances effectiveness.

Example 2

Analysis of the Expression Function of HM1.24 Antigen by the Reporter Gene Analysis In order to investigate whether the expression induction of antigen is regulated by the HM1.24 promoter region, the reporter gene at the promoter region was analyzed.

The gene (SEQ ID NO: 3) of the HM1.24 promoter region was obtained by PCR cloning. Genomic DNA was prepared from human peripheral blood mononuclear cells using the DNAzol reagent (GIBCO). With the genomic DNA obtained as the template, using primer HM2k (aaaggtaccagctgtctttct-gtctgtcc)(SEQ ID NO: 5) and BST2B (atagtcatacgaagtagat-gccatccag) (SEQ ID NO: 6), PCR (94° C. for 1 min, 55° C. for 1 min, 72° C. for 1 min, 30 cycles) was performed using TaKaRa Taq (Takara Shuzo, Ohtsu) in a Thermal Cycler 480 (Perkin-Elmer, Calif., USA).

An about 2 kb fragment obtained was treated with restriction enzymes KpnI and BglII (Takara Shuzo), and was cloned into the KpnI-BglII site of a reporter gene plasmid pGL3-basic (Promega, Wis., USA) using the DNA ligation kit ver. II (Takara Shuzo) to transform into competent E. coli JM109 (Nippongene). The transformed E. coli was cultured at 37° C. in the LB medium containing 100 μ/ml ampicillin, and the plasmid was prepared using the QIAGEN plasmid maxi kit (QIAGEN, Hilden, Germany).

The plasmid HM-2k/GL3 obtained was treated with restriction enzymes KpnI and XhoI, from which a deletion clone was constructed using the deletion kit (Takara Shuzo) for a kilo-sequence to obtain a plasmid HM-493/GL3 containing from the transcription initiation point to 493 bp upstream. Furthermore, HM-2k/GL3 was treated with restriction enzymes KpnI and AflII, from which a deletion clone was constructed as described above, and HM-151/GL3 and HM-77/GL3 containing from the transcription initiation point to −151 bp or −77 bp upstream.

For the introduction of the plasmid into the cell, the polyethyleneimine-Transferrinfection Kit (Tf PEI-Kit) (Bender MedSystems, Vienna, Austria) was used, and for the luciferase assay the Dual-Luciferase Reporter Assay System (Promega) was used. The cell line was cultured overnight in RPMI-1640 medium containing 50 μM Defferrioxamine and 10% FBS. In order to form a complex of the plasmid to be introduced with Tf-PEI, a mixture of the reporter gene plasmid at a final concentration of 20 μg/ml, 0.4 μg/ml of pRL-SV40, and 1 μg/ml of Tf-PEI reagent was prepared and was incubated at room temperature for 20 minutes. $5\times10^5$ cells/ml of cells were added at three volumes of the Tf-PEI/plasmid mixture, and was incubated at 37° C. for four hours, washed with the medium, and 100 μl per well at a concentration of $2\times10^5$ cells/ml was cultured in a 96-well flat-bottomed plate.

IFN-α was added to a final concentration of 0, 10, 100, or 1000 U/ml, which was cultured at 37° C. for two days. After the cells were washed in PBS(−), they were dissolved in 20 μl of the Passive Lysis Buffer, six μl of which was applied to the C96 White Polysorp Fluoronunc plate (Nunc). Using the LUMINOSKAN (Labsystems), luminescence intensity was measured for Firefly and Renila at 30 μl of the substrate solution and a measurement time of 10 seconds. The measured values were corrected by Firefly/Renila, and the relative activity was determined with the control (medium) as one.

Figure 3:
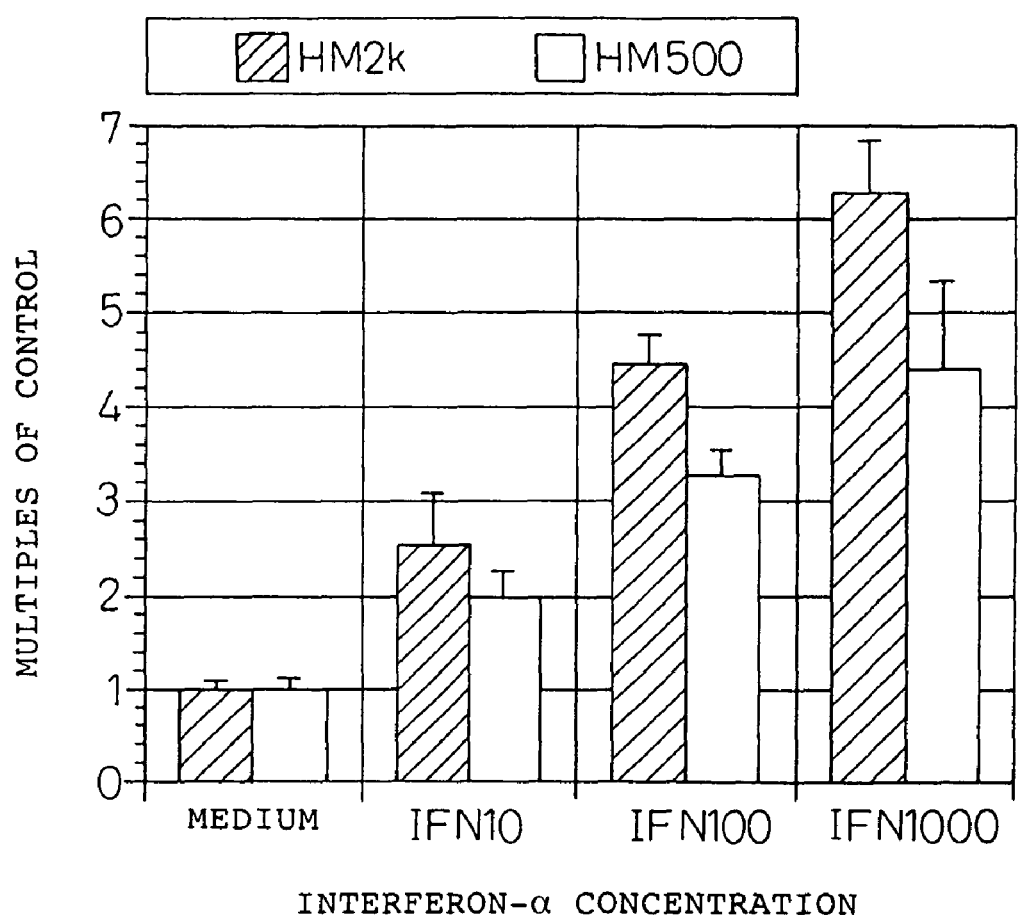
FIG. 3 is a graph showing the result of an experiment in which the U266 cells transformed with a reporter plasmid into which the promoter region of the gene encoding HM1.24 antigen has been inserted were cultured in the absence of interferon-α or in the presence of various concentrations thereof, and then the luciferase activity was determined.

As a result, the luciferase activity of the reporter was increased in a IFN-α concentration dependent manner for both of the upstream 2 kbp and 493 bp, confirming that the enhanced transcription activity of the promoter region causes the expression induction of the antigen (FIG. 3).

Figure 4:
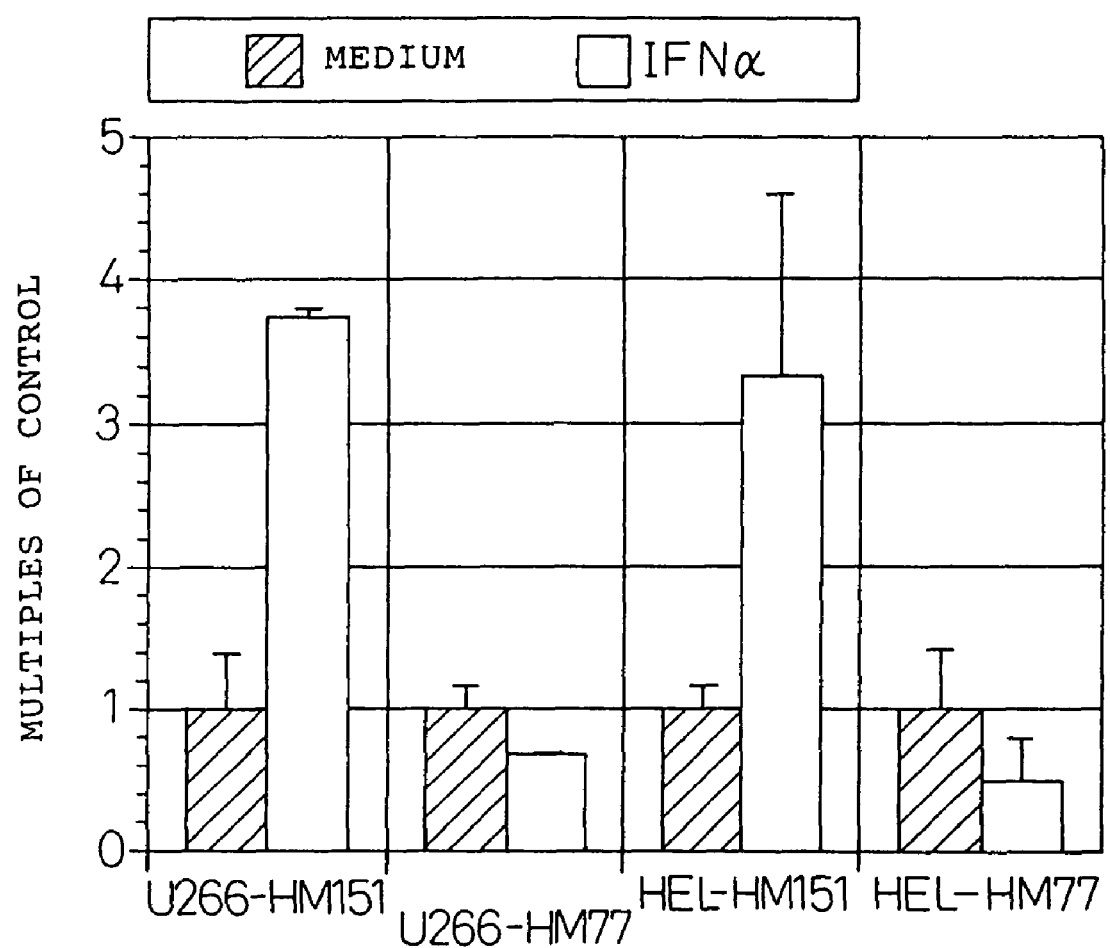
FIG. 4 is a graph showing the result of an experiment in which the U266 cells or the HEL cells transformed with a reporter plasmid into which the segment from the transcription initiation point to 151 bp upstream or to 77 bp upstream among the promoter region of the gene encoding HM1.24 antigen has been inserted were cultured in the presence of interferon-α, (1000 U/ml), and then the luciferase activity was determined.

Furthermore, the result of an experiment in which the upstream 151 bp and 77 bp reporter plasmid of the transcription initiation point were used, an enhanced luciferase activity by IFN-α stimulation was observed for the upstream 151 bp reporter plasmid. On the other hand, no changes in activity were noted by IFN-α stimulation in the upstream 77 bp reporter plasmid (FIG. 4). In the region of 77-151 bp, a sequence having a high homology with GAS element and ISRE was present and, as it is a transcription regulatory factor that is activated in response to IFN-α stimulation, the transcription regulatory factor of the IRF family was shown to be involved in the activity.

Example 3

Enhancement of the Amount Expressed of HM1.24 Antigen in Myeloma Cells by Interferon-γ

Figure 5:
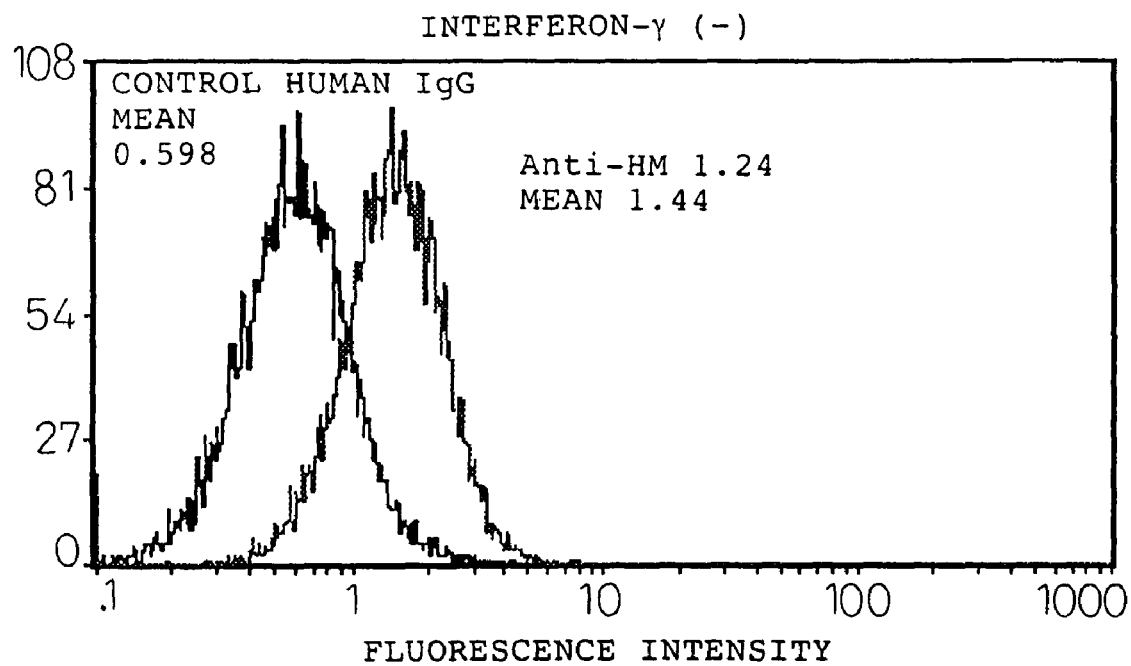
FIG. 5 shows the result of an experiment in which a myeloma cell line U266 cultured in the absence (upper) or presence (bottom) of interferon-γ was analyzed by flow cytometry using human IgG (control) or anti-HM1.24 antibody as a label.
Figure 5:
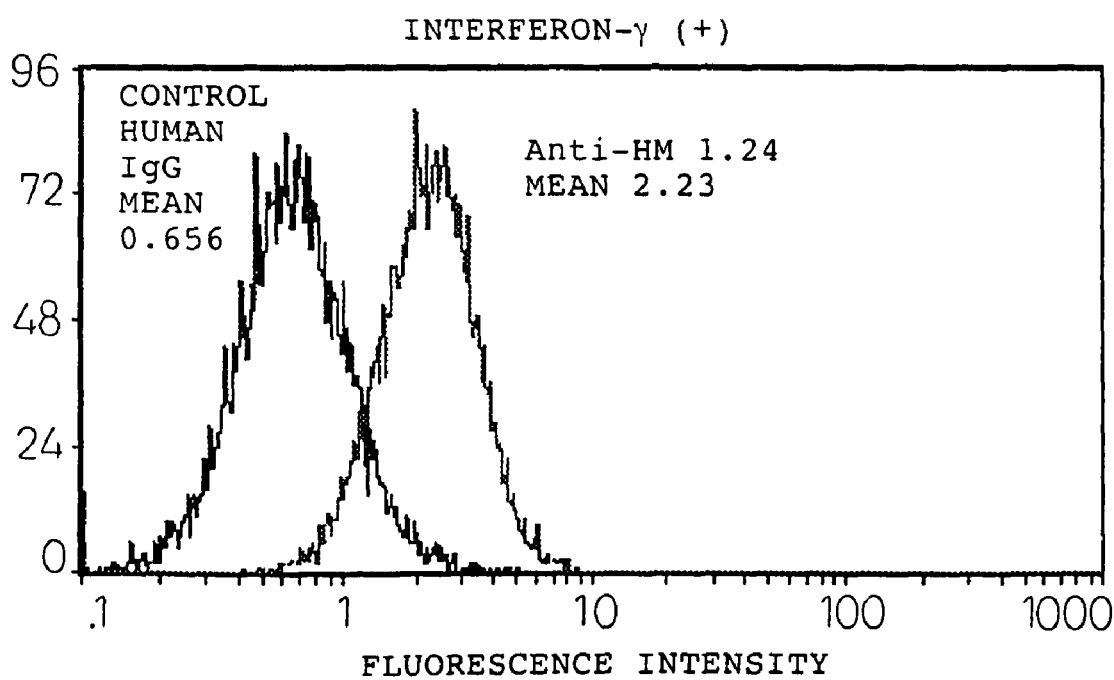
Figure 6:
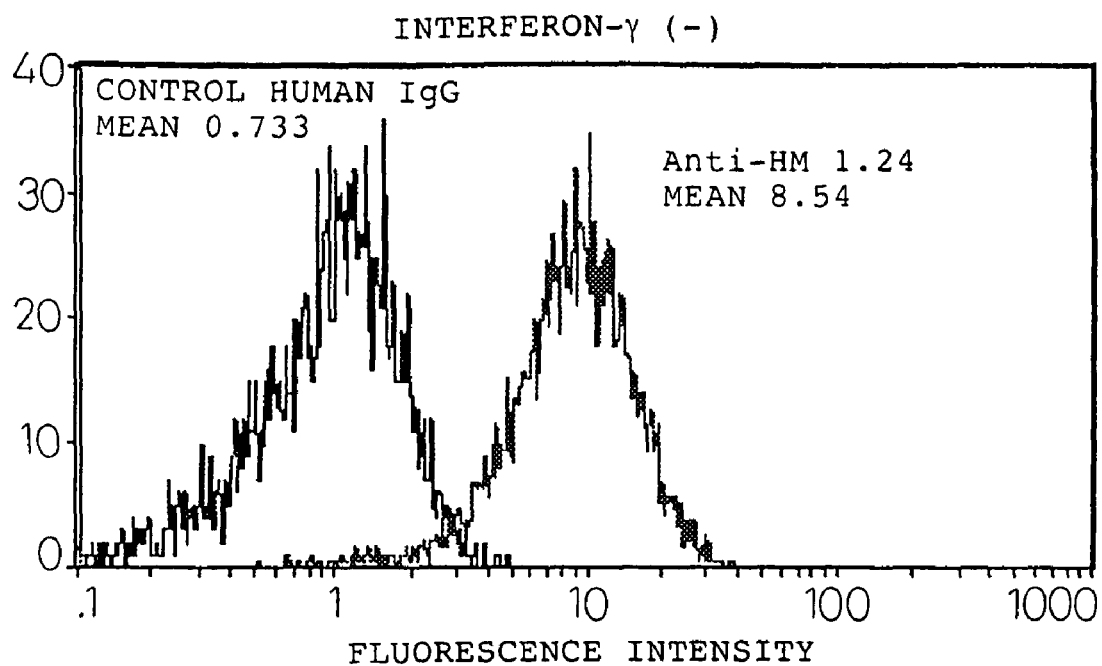
FIG. 6 shows the result of an experiment in which the myeloma cells of the patient cultured in the absence upper) or presence (bottom) of interferon-γ was analyzed by flow cytometry using human IgG (control) or anti-HM1.24 antibody as a label.
Figure 6:
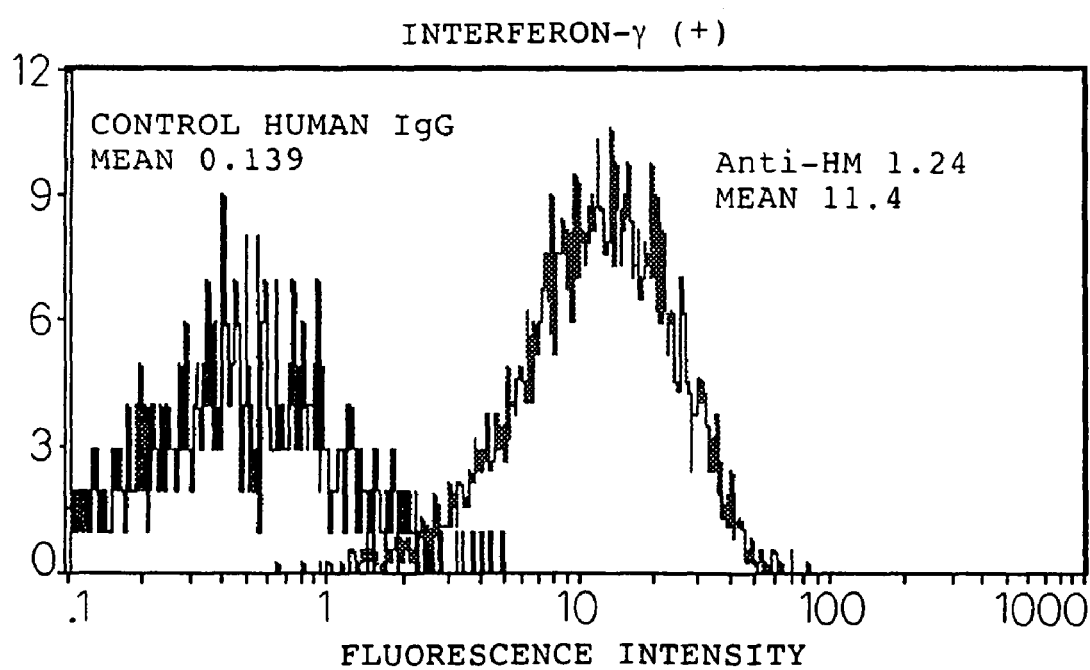

According to the method described in Example 1, 1000 U/ml of the natural type interferon-γ (R & D System) was used for analysis. As a result, increases in the amount expressed of HM1.24 antigen were observed in both of the myeloma cell line U266 (FIG. 5) and the patient's myeloma cells (FIG. 6) as for interferon-α.

Example 4

Binding of IRF-2 to the HM1.24 Promoter Region

In order to identify the transcription factor that binds to the HM1.24 promoter region, the Electrophoresis Mobility Shift Assay (EMSA) with the HM1.24 promoter region as the probe was performed as follows to identify IRF-2 as the binding factor.

(1) Preparation of Nuclear Extract

The myeloma cells U266-B1 (ATCC-TIB196) were cultured in the RPMI-1640 medium (GIBCO-BRL) containing 10% FBS (HyClone) at 37° C. in a 5% $CO_2$ incubator. In order to stimulate the cells by interferon-α (IFN-α) (Pepro Tech EC), IFN-α was added to the medium to a final concentration of 1000 U/ml, and the cells were recovered at 30 minutes, two hours, four hours, and eight hours after the addition. The cells were suspended into cold PBS (−), centrifuged at 1,000 rpm to discard the supernatant, and suspended in a 10 mM Tris, 10 mM NaCl, and 6 mM $MgCl_2$ solution.

After allowing to stand in ice for five minutes, centrifugation was repeated, and the supernatant was discarded. The cells were suspended into 10 mM Tris, 10 mM NaCl, 6 mM $MgCl_2$, 1 mM DTT, 0.4 mM PMSF, 1 mM $Na_3VO_4$. The cells were homogenized on ice using a glass homogenizer, centrifuged at 6000 g for three minutes, and the supernatant was discarded. The cells were suspended into the extraction buffer (20% glycerol, 20 mM HEPES, 420 mM NaCl, 1.5 mM $MgCl_2$, 0.2 mM EDTA, 0.2 mM PMSF, 1 mM DTT, 0.1 mM $Na_3VO_4$, 2 mg/ml aprotinin, and 5 mg/ml leupeptin), and then was allowed to stand in ice for 20 minutes. It was centrifuged at 12000 g for 10 minutes, and the supernatant was recovered.

(2) Preparation of the Labeled Probe

As the probe, ISRE2 was constructed that contains a sequence (ttcccagaaa (SEQ ID NO: 11)) having a homology with GAS (IFN-γ activation site: the GAS consensus sequence is ttncnnnaa (SEQ ID NO: 9)) and ISRE (IFN-α stimulation response factor: the ISRE consensus sequence is ngaaanngaaact (SEQ ID NO: 10)), and ggaaactgaaact (SEQ ID NO: 12) at the HM1.24 promoter region. Thus, oligo DNA ISRE-F2 (aatttctgggaaactgaaactgaaaacct(SEQ ID NO: 13)) and ISRE-R2 (aattaggttttcagtttcagtttcccaga(SEQ ID NO: 14)) were mixed and annealed to form a double stranded DNA probe ISRE2.

Furthermore, oligo DNA adp-1 (catggcatctacttcgtatgactat-tgcagagtgcc(SEQ ID NO: 15)) and adp-2 (catgggcactctgcaat-agtcatacgaagtagatgc (SEQ ID NO: 16)) were mixed and annealed to form an unrelated probe adp. Probes were labeled using the Band Shift Kit (Amersham Pharmacia Biotech) according to the standard protocol. Thus, 50 ng of double stranded DNA constructed as above was subjected to the polymerase reaction of the Klenow fragment in a reaction solution containing DATP (20 µCi) (Amersham Pharmacia Biotech) at 37° C. for one hour. The solution that completed the reaction was diluted two-fold and then was loaded to the Nick Spin Column (Amersham Pharmacia Biotech), and after centrifugation at 1600 rpm for four minutes, the solution was recovered to prepare a labeled probe.

(3) Changes with Time in the Binding Factor Produced by Stimulation of IFN-α

According to the standard protocol of the Band Shift Kit (Amersham Pharmacia Biotech, N.J., USA), the following procedure was performed. To 5 µg of the extracts temporally prepared in the above (1) were added 2 µl of the 10× binding buffer (100 mM Tris-HCl, pH 7.5, 500 mM NaCl, 5 mM DTT), 4 µl of 50% glycerol, 1 µl of 1% NP-40, and 1 µl of poly(dI-dC)/poly(dI-dC), and 2 µl of the $^{32}P$ labeled ISRE-2 probe prepared in the above (2) was added, to which water was added to a total volume of 20 µl, and this reaction mixture was incubated at room temperature for 20 minutes to allow for the binding of the possible binding factors that may be present in the above extract and said $^{32}P$ labeled ISRE-2 probe.

To 18 µl of the reaction mixture was added 2 µl of the 10× stain solution (attached to the kit), which was electrophoresed in 1× Tris-glycine buffer (25 mM Tris, 190 mM glycine, 1 mM EDTA, pH 8.1) on a 7.5% acrylamide gel, and then, after electrophoresis, the gel was attached to the filter paper to transfer protein to the filter paper. The filter paper dried with a gel drier was exposed to X-ray film to detect signals.

For comparison, a reaction solution [(NEC—)] to which no extract was added, a reaction solution [0h] to which an extract from the cell culture that was cultured without stimulation by interferon-α was added, a reaction solution [8h (+cold)] in which 50 ng of a nonlabeled ISRE2 probe was added instead of the labeled probe to the extract of 8 hour-culture, and a reaction solution [8h (+cold unrelated)] in which 50 ng of an unrelated probe adp was added to the extract of 8 hour-culture were prepared, and were processed as described above to detect signals.

Figure 7:
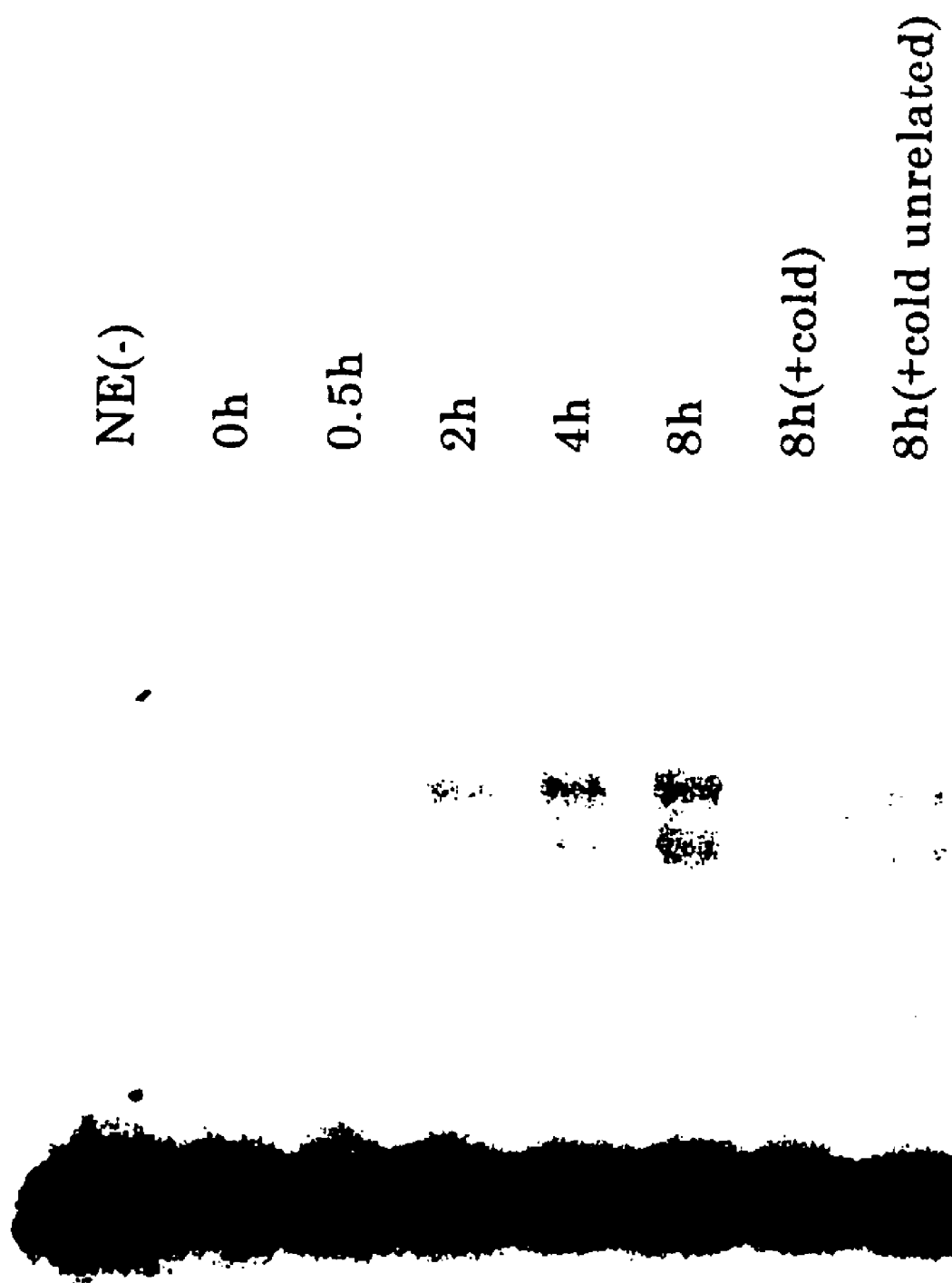
FIG. 7 is an electrophoretogram that shows changes with time in the amount of transcription factors that are produced by adding IFN-α to the cultured U266 cells and that bind to the HM1.24 promoter region, and is a photograph substituted for drawing. NE(−): no nuclear extract was added. 0 h: the nuclear extract without IFN-α stimulation was added. 0.5-8 h: the nuclear extract for which the respective time elapsed after stimulation with IFN-α (1000 U/ml) was added. +cold: 50 ng of the nonlabeled ISRE2 probe was added. +cold unrelated: 50 ng of the nonlabeled adp sequence was added.

The result is shown in FIG. 7. As can be seen from this figure, a substance that binds to a double stranded DNA corresponding to part of the HM1.24 promoter increased with time in the U266-B1 cells cultured under the stimulation by interferon.

(4) The Identification of a Transcription Factor by Reaction with Various Antibodies In a manner similar to that described in the above (1), the myeloma cells U266-B1 (ATCC-TIB196) were cultured for eight hours in the presence of 1000 U/ml of interferon-α to prepare an extract. The following procedure was performed according to the standard protocol of the Band Shift Kit (Amersham Pharmacia Biotech). Thus, 2 µg of antibody was added to 5 µg of the extract, and incubated at room temperature for 15 minutes to obtain an extract/antibody reaction solution. TO 2 µl of the 10× binding buffer attached to the kit, 4 µl of 50% glycerol, 1 µl of 1% NP-40, and 1 µl of Poly(dI-dC)/Poly(dI-dC)were added 2 µl of the above extract/antibody reaction solution and 2 µl of the labeled probed prepared in the above (2), to which water was added to make the total volume 20 µl, and the reaction mixture was incubated at room temperature for 20 minutes.

The reaction mixture was subjected to electrophoresis as described in the above (3) to detect signals.

As the above antibody, the following antibodies (all are from Santa Cruz Biotechnology) were used:

Anti-human STAT1 p84/p91 (E-23): (description) rabbit polyclonal antibody (SC-346X)

Anti-human STAT2 (C-20): rabbit polyclonal antibody (SC-476X)

Anti-mouse STAT3 (K-15): rabbit polyclonal antibody (SC-483X)

Anti-human ISGF-3γ p48 (C-20): rabbit polyclonal antibody (SC-496X)

Anti-human IRF-1 (C-20): rabbit polyclonal antibody (SC-497X)

Anti-human IRF-2 (C-19): rabbit polyclonal antibody (SC-498X)

Anti-mouse ICSAT (M-17): rabbit polyclonal antibody (SC-6059X)

AS a control, a reaction solution that uses an extract of the cells cultured without interferon stimulation [0h]; a reaction solution in which an extract of the cells cultured for eight hours under the stimulation of 1000 U/ml interferon-α was added, and no antibody was added [8h]; a reaction solution in which 50 ng of the nonlabeled ISRE2 probe was added the labeled ISRE2 [8h (+cold)]; a reaction solution in which 50 ng of the nonlabeled dp probe was added the labeled ISRE2 probe [8h (+cold)] and were prepared, and were processed as described above.

Figure 8:
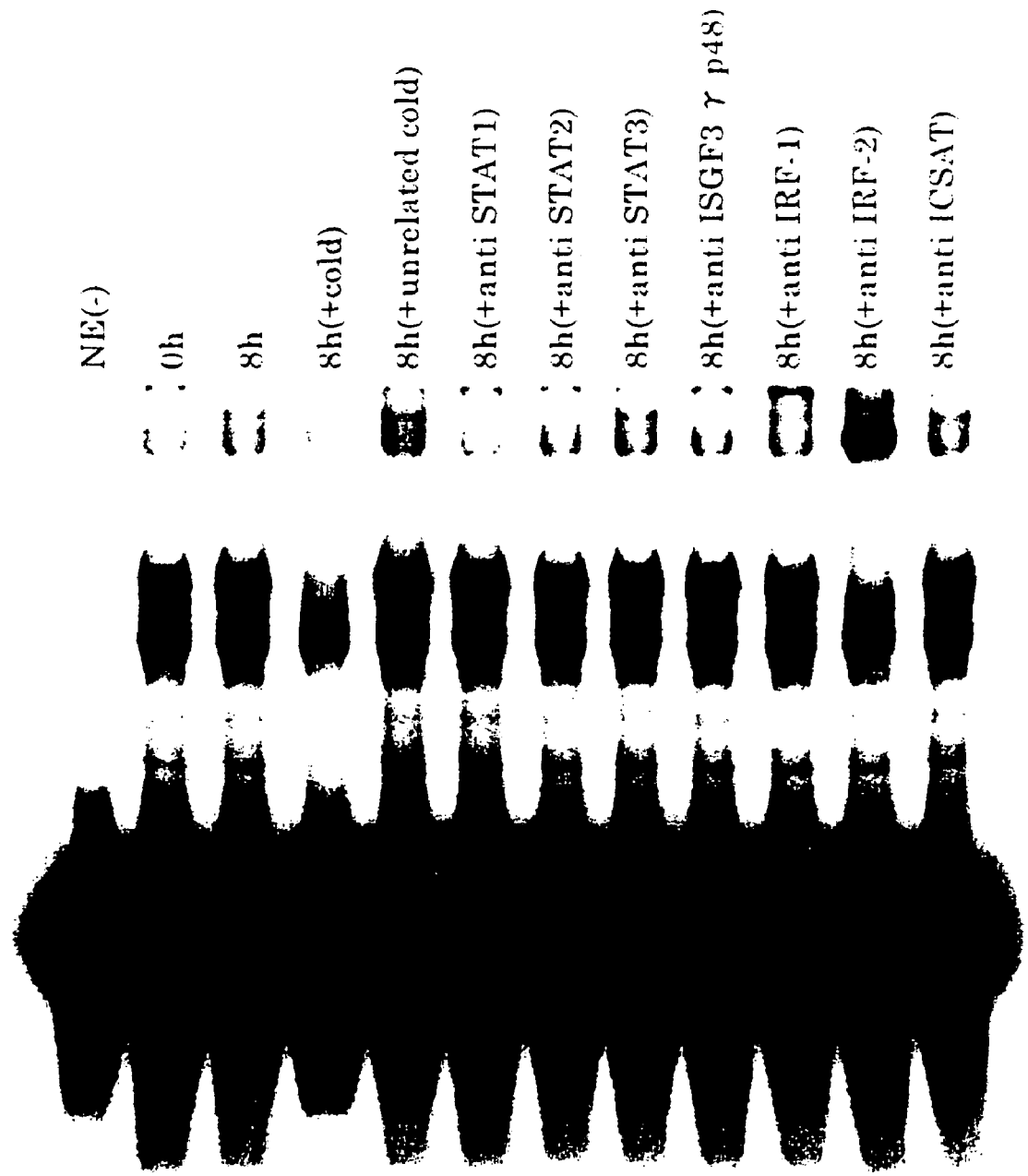
FIG. 8 is an electrophoretogram showing the result of an experiment in which the transcription factors that bind to HM1.24 promoter were identified using various antibodies, and is a photograph substituted for drawing. NE(−): no nuclear extract was added. 0 h: the nuclear extract without IFN-α stimulation was added. 8 h: the nuclear extract for which the respective time elapsed after stimulation with IFN-α (1000 U/ml) was added. +cold: 50 ng of the nonlabeled ISRE2 probe was added. +cold unrelated: 50 ng of the nonlabeled adp sequence was added. Two μg each of antibodies was added.

The result is shown in FIG. 8. As can be seen from this figure, it was shown that the component that binds to the labeled ISRE2 probe in the extract from the cells cultured under the stimulation of interferon-α binds only to anti-IRF-2 antibody, and the factor that binds to and thereby activates the HM1.24 promoter is a transcription factor IRF-2.

Example 5

Confirmation of the HM1.24 Promoter Activation with IRF-2

Effect on HM1.24 promoter activity by IRF-2 co-expression was determined by the reporter gene assay using the U266 cells, and it was revealed that IRF-2 actually has the transcription activation activity of the HM1.24 promoter. In the following experiment, a myeloma cell line U266-B1 (ATCC TIB196) was used. The cells were cultured in the RPMI-1640 medium (GIBCO) (referred to hereinafter as the medium) containing 10% FBS (GIBCO BRL) in an 5% $CO_2$ incubator.

(1) Construction of a Plasmid Containing the HM1.24 Promoter Region

The gene of the HM1.24 promoter region was obtained by PCR cloning. From human peripheral blood mononuclear cells, genomic DNA was prepared using the DNAzol reagent (GIBCO). With the genomic DNA obtained as the template, using primer HM2k (aaaggtaccagctgtctttctgtctgtcc) (SEQ ID NO: 17) and BST2B (atagtcatacgaagtagatgccatccag) (SEQ ID NO: 18), PCR (94° C. for 1 min, 55° C. for 1 min, 72° C. for 1 min, 30 cycles) was performed using TaKaRa Taq (Takara Shuzo, Ohtsu) in the Thermal Cycler 480 (Perkin-Elmer, Calif., USA).

An about 2 kb fragment obtained was treated with restriction enzymes KpnI and BglII (Takara Shuzo), and was cloned into the KpnI-BglII site of a reporter gene plasmid pGL3-basic (Promega, Wis., USA) using the DNA ligation kit ver. II (Takara Shuzo) to transform competent *E. coli* JM109 (Nippongene). The transformed *E. coli* was cultured at 37° C. in the LB medium containing 100 μg/ml ampicillin, and a plasmid was prepared using the QIAGEN plasmid maxi kit (QIAGEN, Hilden, Germany).

The plasmid HM-2k/GL3 obtained was treated with restriction enzymes KpnI and XhoI, from which a deletion clone was constructed using the deletion kit for kilo-sequencing (Takara Shuzo) obtain a plasmid HM-491/GL3 containing up to −491 bp upstream of the transcription initiation point. Furthermore, HM-2k/GL3 was treated with restriction enzymes KpnI and AflII, from which a deletion clone was constructed as described above, and HM-151/GL3 containing −151 bp upstream of the transcription initiation point.

Furthermore, with HM-2k/GL3 as the template, using primer 10S (tttcggtacctaattaatcctctgcctg) (SEQ ID NO: 19) and GL primer 2 (ctttatgttttggcgtcttcca) (SEQ ID NO: 20), PCR (94° C. for 1 min, 55° C. for 1 min, 72° C. for 1 min, 30 cycles) was performed using TaKaRa Taq (Takara Shuzo, Ohtsu) in a Thermal Cycler 480 (Perkin-Elmer, Calif., USA). The fragment obtained was treated with restriction enzymes KpnI and BglII (Takara Shuzo), and was cloned into the KpnI-BglII site of a reporter gene plasmid pGL3-basic (Promega, Wis., USA) using the ligation high (Toyobo) to transform competent *E. coli* JM109 (Nippongene).

The transformed *E. coli* was cultured at 37° C. in the LB medium containing 100 μg/ml ampicillin, and a plasmid was prepared using the QIAGEN plasmid maxi kit (QIAGEN, Hilden, Germany). A plasmid HM-125/GL3 was thus obtained that contains up to 125 bp upstream of the transcription initiation point. Furthermore, with HM-2k/GL3 as the template, using primer HMP700(aaaggtaccagagtttacctggtatcctgg) (SEQ ID NO: 21) and GL primer 2, PCR was performed in a similar procedure and, by introducing the fragment into the KphI-BglII site of pGL3-basic, HM-700/GL3 containing up to about 700 bp upstream of the transcription initiation point was obtained.

Furthermore, with HM-2k/GL3 as the template, using primer HMP700 and 11A' (cagaggattaattaggtaccgaaagagaggtgggctttt) (SEQ ID NO: 22), PCR (98° C. for 15 seconds, 65° C. for 2 seconds, 74° C. for 30 seconds, 25 cycles) was performed using the KOD polymerase (Toyobo) in a Thermal Cycler 480 (Perkin-Elmer, Calif., USA). The fragment obtained was inserted into the pCR4 Blunt-TOPO vector using the Zero Blunt TOPO PCR cloning kit for sequencing ver. B (Invitrogen). The plasmid obtained was treated with a restriction enzyme KpnI, and an about 550 bp fragment was recovered, which was introduced into the KpnI site of HM-125/GL3 using the "ligation high". Thus, dISRE/GL3 lacking −25 to −145 upstream of the transcription initiation point was obtained.

(2) Construction of IRF-2 Expression Plasmid A4

The IRF-2 expression plasmid was constructed as follows. From the U266 cells, after eight hours have elapsed after stimulation with interferon-α (1000 U/ml), total RNA was extracted using the TRIZOL reagent (GIBCO BRL). With RNA obtained by using the FIRST-STRAND cDNA Synthesis kit (Pharmacia) as the template, and using NotI-d$(T)_{18}$ as the primer, a reverse transcription reaction was performed at 37° C. for one hour. With the cDNA obtained as the template, using IRF2-F2 (ttgtattggtagcgtgaaaaaagc)(SEQ ID NO: 23) and IRF2-R2 (cagctagttcacattatctcgtcc)(SEQ ID NO: 24) as primers, PCR (94° C. for 45 seconds, 60° C. for 45 seconds, 72° C. for 60 seconds, 40 cycles) was performed using LA-TAQ (Takara Shuzo).

With the PCR reaction as the template, using IRF2-F1 (agagggtaccatgccggtggaaaggatgcg) (SEQ ID NO: 25) and IRF2-R1 (agtcggtaccttaactgctcttgacgcggg) (SEQ ID NO: 26) as primers, PCR (94° C. for 45 seconds, 60° C. for 45 seconds, 72° C. for 60 seconds, 30 cycles) was performed using the KOD polymerase (Toyobo). The fragment obtained was treated with a restriction enzyme KpnI, and then introduced into the KpnI site of an expression plasmid pTracer-CMV (Invitrogen) using the ligation high (Toyobo) to obtain an IRF-2 expression plasmid pIRF-2/Tracer.

(3)Measurement of the Reporter Gene Activity

For the introduction of the plasmid into the cells, the polyethyleneimine-Transferrinfection Kit (Tf PEI-Kit) (Bender MedSystems, Vienna, Austria) was used, and for the luciferase assay the Dual-Luciferase Reporter Assay System (Promega) was used. The cell line was cultured overnight in RPMI-1640 containing 50 μm Defferrioxamine and 10% FBS. In order to form a complex of the plasmid to be introduced with Tf-PEI, a mixture of the reporter gene plasmid at a final concentration of 20 μg/ml, 20 μg/ml of pIRF-2/Tracer or pTracer-CMV, 0.4 μg/ml of pRL-SV40, and 1 μg/ml of Tf-PEI reagent was prepared and was incubated at room temperature for 20 minutes. A5

5×10⁵ cells/ml of cells were added at three volumes of the Tf-PEI/plasmid mixture, and was incubated at 37° C. for four hours, washed with the medium, and 100 μl per well at a concentration of 2×10⁵ cells/ml was cultured in a 96-well flat-bottomed plate. IFN-α was added to a final concentration of 0 or 1000 U/ml, which was cultured at 37° C. for two days. After the cells were washed in PBS(−), it was dissolved in 20 μl of the Passive Lysis Buffer, six μl of which was applied to the C96 White Polysorp Fluoronunc plate (Nunc). Using the LUMINOSKAN (Labsystems), luminescence intensity was measured for Firefly and Renila at 30 μl of the substrate at a measurement time of 10 seconds. The measured values were corrected by Firefly/Renila to obtain the correct relative activity.

(4) Result

Figure 9:
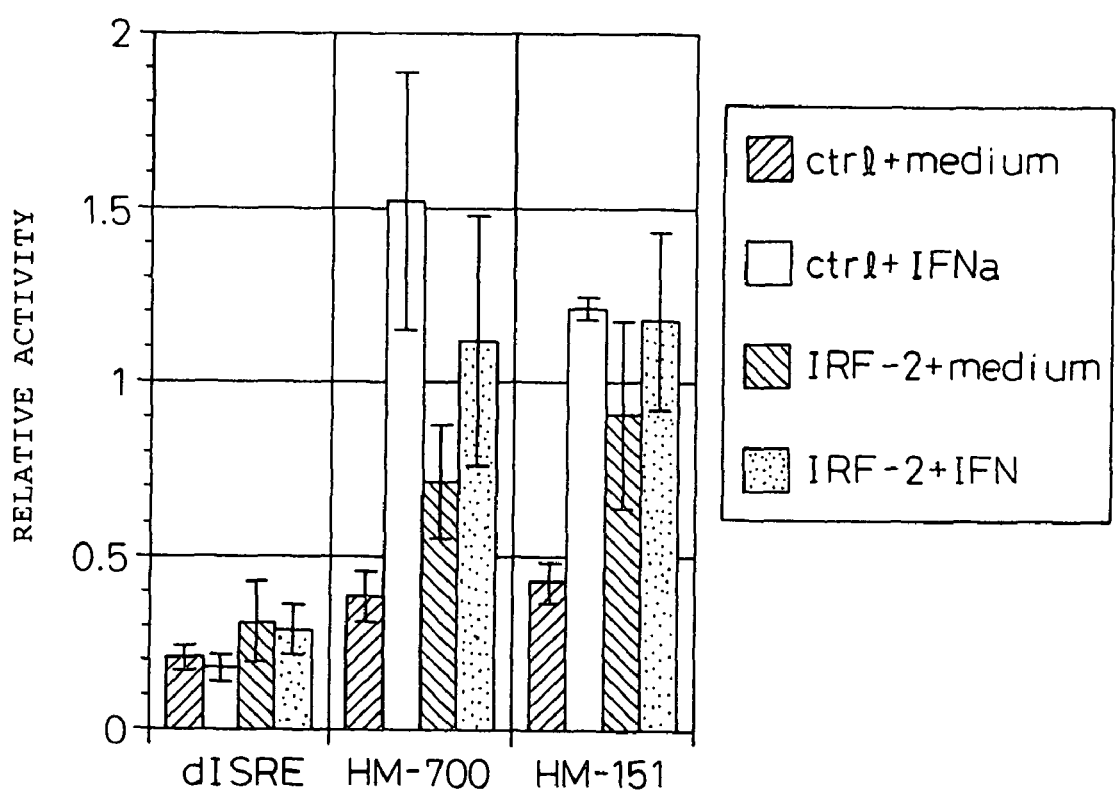
FIG. 9 is a graph showing the result of an experiment in which the HM1.24 promoter reporter plasmid and the IRF-2 expression plasmid were introduced into the U266 cells, and the reporter activity was determined.

The HM1.24 promoter reporter plasmid and the IRF-2 expression plasmid were introduced into the U266 cells, and the reporter activity was determined (FIG. 9). As a result, the luciferase activity was increased in −700 and −151 containing the ISRE motif sequence that is an IRF-2 binding site by IRF-2 co-expression. On the other hand, no changes in activity were noted in dISRE/GL3 that lacks the ISRE sequence by IRF-2 co-expression. This result indicated that IRF-2 binds to the ISRE region of the HM1.24 promoter and enhances its transcription activity.

(5) Confirmation of Enhanced Expression of HM1.24 Antigen by the Forced Expression of IRF-2

For confirmation of change in an amount of expression of HM1.24, by IRF2, the IRF-2 expression plasmid (pIRF-2/Tracer) or the control plasmid (pTracer/CMV) is introduced into the U266 cells in the method described above, and then cultured for 1-2 days, from which the cells are recovered, and then stained with mouse anti-human HM1.24 antibody as a primary antibody. The cells are washed, and further stained with FITC-labeled anti-mouse IgG antibody as a secondary antibody. After washing the cells, the FITC fluorescence intensity of the cells is measured by flow cytometry. It is confirmed that, in the cells in which the IRF-2 expression plasmid was introduced, there are more cells having a high FITC intensity compared to the cells in which the control plasmid was introduced.

Reference to the microorganisms deposited under the Patent Cooperation Treaty, Rule 13-2, and the name of the Depository organ Depository Organ
Name: the National Institute of Bioscience and Human Technology, Agency of Industrial Science and Technology
Address: 1-3, Higashi 1-chome, Tsukuba city, Ibaraki Pref., Japan Organism (1)
Name: *Escherichia coli* DH5α (pRS38-pUC19)
Accession number: FERM BP-4434
Date deposited: Oct. 5, 1993

Organism (2)
Name: Mouse-mouse hybridoma HM1.24
Accession number: FERM BP-5233
Date deposited: Apr. 27, 1995

Organism (3)
Name: *Escherichia coli* DH5α (pUC19-RVHr-AHM-gγl)
Accession number: FERM BP-5643
Date deposited: Aug. 29, 1996

Organism (4)
Name: *Escherichia coli* DH5α (pUC19-1.24H-gγl)
Accession number: FERM BP-5644
Date deposited: Aug. 29, 1996

Organism (5)
Name: *Escherichia coli* DH5α (pUC19-RVLa-AHN-gκ)
Accession number: FERM BP-5645
Date deposited: Aug. 29, 1996

Organism (6)
Name: *Escherichia coli* DH5α (pUC19-1.24L-gκ)
Accession number: FERM BP-5646
Date deposited: Aug. 29, 1996

The invention claimed is:

1. A method for treating myeloma comprising:
   enhancing expression of HM1.24 antigen having the sequence as set forth in SEQ ID NO: 2, in myeloma cells by administering interferon regulatory factor-2 protein, and
   administrating an antibody that specifically binds to a protein having the amino acid sequence of SEQ ID NO: 2, wherein a therapeutic anti-tumor effect by the antibody is enhanced by an increased number of anti-HM 1.24 antibodies binding to the myeloma cell.

2. The method according to claim 1, wherein the antibody has cytotoxic activity.

3. The method according to claim 1 or 2, wherein the myeloma is multiple myeloma.

4. The method according to claim 2, wherein the antibody is a monoclonal antibody.

5. The method according to claim 4, wherein the antibody is a chimeric antibody or a humanized antibody.

6. The method according to claim 4, wherein the antibody is anti-HM1.24 antibody.

7. The method according to claim 6, wherein the chimeric antibody or humanized antibody is chimeric anti-HM1.24 antibody or humanized anti-HM1.24 antibody.

* * * * *

SEQUENCE LISTING

```
<160> NUMBER OF SEQ ID NOS: 26

<210> SEQ ID NO 1
<211> LENGTH: 1013
<212> TYPE: DNA
<213> ORGANISM: Homo sapiens
<220> FEATURE:
<221> NAME/KEY: CDS
<222> LOCATION: (23)...(540)

<400> SEQUENCE: 1
gaattcggca cgagggatct gg atg gca tct act tcg tat gac tat tgc aga        52
                         Met Ala Ser Thr Ser Tyr Asp Tyr Cys Arg
                          1               5                   10 gtg ccc atg gaa gac ggg gat aag cgc tgt aag ctt ctg ctg ggg ata       100
Val Pro Met Glu Asp Gly Asp Lys Arg Cys Lys Leu Leu Leu Gly Ile
                 15                  20                  25 gga att ctg gtg ctc ctg atc atc gtg att ctg ggg gtg ccc ttg att       148
Gly Ile Leu Val Leu Leu Ile Ile Val Ile Leu Gly Val Pro Leu Ile
             30                  35                  40 atc ttc acc atc aag gcc aac agc gag gcc tgc cgg gac ggc ctt cgg       196
Ile Phe Thr Ile Lys Ala Asn Ser Glu Ala Cys Arg Asp Gly Leu Arg
         45                  50                  55 gca gtg atg gag tgt cgc aat gtc acc cat ctc ctg caa caa gag ctg       244
```

|  |  |  |  |  |  |  |  |  |  |  |  |  |  |  |  |
|---|---|---|---|---|---|---|---|---|---|---|---|---|---|---|---|
| Ala | Val | Met | Glu | Cys | Arg | Asn | Val | Thr | His | Leu | Leu | Gln | Gln | Glu | Leu |
|  | 60 |  |  |  | 65 |  |  |  | 70 |  |  |  |  |  |  |

```
acc gag gcc cag aag ggc ttt cag gat gtg gag gcc cag gcc gcc acc      292
Thr Glu Ala Gln Lys Gly Phe Gln Asp Val Glu Ala Gln Ala Ala Thr
 75              80                  85                  90 tgc aac cac act gtg atg gcc cta atg gct tcc ctg gat gca gag aag      340
Cys Asn His Thr Val Met Ala Leu Met Ala Ser Leu Asp Ala Glu Lys
                 95                 100                 105 gcc caa gga caa aag aaa gtg gag gag ctt gag gga gag atc act aca      388
Ala Gln Gly Gln Lys Lys Val Glu Glu Leu Glu Gly Glu Ile Thr Thr
                110                 115                 120 tta aac cat aag ctt cag gac gcg tct gca gag gtg gag cga ctg aga      436
Leu Asn His Lys Leu Gln Asp Ala Ser Ala Glu Val Glu Arg Leu Arg
            125                 130                 135 aga gaa aac cag gtc tta agc gtg aga atc gcg gac aag aag tac tac      484
Arg Glu Asn Gln Val Leu Ser Val Arg Ile Ala Asp Lys Lys Tyr Tyr
        140                 145                 150 ccc agc tcc cag gac tcc agc tcc gct gcg gcg ccc cag ctg ctg att      532
Pro Ser Ser Gln Asp Ser Ser Ser Ala Ala Ala Pro Gln Leu Leu Ile
155                 160                 165                 170 gtg ctg ct gggcctcagc gctctgctgc agtgagatcc caggaagctg gcacatcttg    590
Val Leu gaaggtccgt cctgctcggc ttttcgcttg aacattccct tgatctcatc agttctgagc    650
gggtcatggg gcaacacggt tagcggggag agcacggggt agccggagaa gggcctctgg    710
agcaggtctg gaggggccat ggggcagtcc tgggtctggg gacacagtcg ggttgaccca    770
gggctgtctc cctccagagc ctccctccgg acaatgagtc cccctcttg tctcccaccc     830 tgagattggg catggggtgc ggtgtggggg gcatgtgctg cctgttgtta tgggtttttt    890
ttgcgggggg ggttgctttt ttctggggtc tttgagctcc aaaaaaataa acacttcctt    950
tgagggagag cacaccttaa aaaaaaaaa aaaaaaaaa aaaaaaaat tcgggcggcc      1010 gcc                                                                1013
```

<210> SEQ ID NO 2
<211> LENGTH: 172
<212> TYPE: PRT
<213> ORGANISM: Homo sapiens
<220> FEATURE:
<221> NAME/KEY: SIGNAL
<222> LOCATION: (1)...(1)

<400> SEQUENCE: 2

```
Met Ala Ser Thr Ser Tyr Asp Tyr Cys Arg Val Pro Met Glu Asp Gly
 1               5                  10                  15

Asp Lys Arg Cys Lys Leu Leu Leu Gly Ile Gly Ile Leu Val Leu Leu
                20                  25                  30

Ile Ile Val Ile Leu Gly Val Pro Leu Ile Ile Phe Thr Ile Lys Ala
             35                  40                  45

Asn Ser Glu Ala Cys Arg Asp Gly Leu Arg Ala Val Met Glu Cys Arg
         50                  55                  60

Asn Val Thr His Leu Leu Gln Gln Glu Leu Thr Glu Ala Gln Lys Gly
 65                  70                  75

Phe Gln Asp Val Glu Ala Gln Ala Ala Thr Cys Asn His Thr Val Met
80                  85                  90                  95

Ala Leu Met Ala Ser Leu Asp Ala Glu Lys Ala Gln Gly Gln Lys Lys
                100                 105                 110

Val Glu Glu Leu Glu Gly Glu Ile Thr Thr Leu Asn His Lys Leu Gln
                115                 120                 125
```

```
Asp Ala Ser Ala Glu Val Glu Arg Leu Arg Arg Glu Asn Gln Val Leu
        130                 135                 140

Ser Val Arg Ile Ala Asp Lys Lys Tyr Tyr Pro Ser Ser Gln Asp Ser
145                 150                 155

Ser Ser Ala Ala Ala Pro Gln Leu Leu Ile Val Leu
160                 165                 170

<210> SEQ ID NO 3
<211> LENGTH: 2061
<212> TYPE: DNA
<213> ORGANISM: Homo sapiens
<220> FEATURE:
<221> NAME/KEY: misc_feature
<222> LOCATION: (1)...(2061)
<223> OTHER INFORMATION: Nucleotide sequence of promoter region of gene
      encoding for HM1.24 protein antigen.
<220> FEATURE:
<221> NAME/KEY: CDS
<222> LOCATION: (2041)...(2061)

<400> SEQUENCE: 3
```

| | | | | | |
|---|---|---|---|---|---|
| actaaaagtc | tctgatatgc | agaaataatg | gcataagctg | tctttctgtc | tgtccctct | 60 |
| ctctctctct | gcctcggctg | ccaggcaggg | aagggccccc | tgtccagtgg | acacgtgacc | 120 |
| cacatgacct | tacctatcat | tggagatgac | tcacactctt | taccctgccc | cttttgcttt | 180 |
| gtatccaata | aataacagca | cagccagaca | ttcggggcca | ctaccagtct | ccgcgcattg | 240 |
| ctggtagtgg | tcccccgggc | ccagctgtct | tttcttttat | ctcttcgtct | tgtgtcttta | 300 |
| tttctacact | ctctcgtcgc | cgcacacagg | gagagaccca | ctgaccctgt | ggggctggtc | 360 |
| cctacagtaa | ttttaaaggg | aagagcaaca | aactttcggt | ttgcagggct | gggactgttt | 420 |
| acagctgcaa | aatttagaga | ggacatcaat | ctattattat | ccacatttta | cagctgggga | 480 |
| aatcaatgct | aagagaggaa | attcatttgc | ccagaggtgc | accacccctgg | cctccaatgt | 540 |
| gcaattcatg | caattgtgat | ttccgacctg | gtcccaaact | aaccctaaag | ttagcaggcc | 600 |
| agaacagtgc | tgctcaaata | agtcagctta | gtcaaataag | tcaggcaaag | gtcgtgtctt | 660 |
| tgcacctgga | gtcctggcca | ggctggtagg | tccctcctcc | tgggacaagt | tcaccctcag | 720 |
| aattttcagc | aagatcatct | cccacagctt | gttaattggt | tcttggttct | aagtgatttt | 780 |
| tttgtttatt | ggtttaagag | atgggatccc | actctatcac | ccaggcttga | gtgccgtggc | 840 |
| acaatcatag | ctcgctgcag | cctcaaactc | ctgggctcga | gtgatcctcc | tgcctcagcc | 900 |
| tcccagcctc | agcctgggac | cacaggcatg | taccaccatg | cctggctcta | agtggcttta | 960 |
| atggggtcct | tctgagggat | gttggagtca | gggcctgggg | ggagttcccc | aggccttctg | 1020 |
| ggaggcctgg | gctctggact | tgacctgcc | tactgtctgg | ccctgctgaa | aagaaaaaaa | 1080 |
| aacatggaaa | tggcagacct | aacagaatct | gggctgtggt | caggatgtgg | ctgaagaagc | 1140 |
| cacaagaaaa | acatgcagtc | ccctttcagc | ggtcatgccc | agcagttggg | tgccgataat | 1200 |
| gggcctgatt | tcctgtagga | agccctggct | ctcttggcca | catggacagt | gtctgaggct | 1260 |
| ggccctgtta | ttcccctttg | cagatgaaga | aacaggctca | gagagtttac | ctggtatcct | 1320 |
| ggagtcccag | gagcactttt | tctggaagta | ggagcttgtt | tcctgcaggt | gccaagacag | 1380 |
| agaccgacat | tgtttgttgg | ctgggtcggt | ctcccagttt | tcagctggct | ccagtctcac | 1440 |
| ctgttgctca | cacaccctcc | atgtctccca | tagtcccctc | ggtggggaca | gaggcactgg | 1500 |
| atgaagccct | gctcgtcacc | acagagacac | ctgaacacaa | aaaccagtcc | ctggggtcag | 1560 |
| acccaggccc | cgccccccaga | cccaggccct | gccctcactc | caccacgcaa | ctgtgcaacc | 1620 |

```
tcagtttccc caggtggaga ccggaccaac aatgatggcc tctgcctctt caggtcatag      1680
tacagatgaa tacaggctgg cacgcctag gcactcagta acacacggca gaggcacagg      1740
gacttaagat ggagtgtccc aggcagccac agttggctgg cacccagttg ggaagggccc      1800
aagggctttt aaagcagggt gaaaaaaaaa gcccacctcc tttctgggaa actgaaactg      1860
aaaacctaat taatcctctg cctgtaggtg cctcatgcaa gagctgctgg tcagagcact      1920
tcctggaact tgctattggt caggacgttt cctatgctaa taaggggtg gcccgtagaa       1980 gattccagca ccctccccta actccaggcc agactccttt cagctaaagg ggagatctgg      2040 atg gca tct act tcg tat gac                                           2061
Met Ala Ser Thr Ser Tyr Asp
 1               5
```

```
<210> SEQ ID NO 4
<211> LENGTH: 7
<212> TYPE: PRT
<213> ORGANISM: Homo sapiens

<400> SEQUENCE: 4

Met Ala Ser Thr Ser Tyr Asp
 1               5

<210> SEQ ID NO 5
<211> LENGTH: 29
<212> TYPE: DNA
<213> ORGANISM: Artificial Sequence
<220> FEATURE:
<223> OTHER INFORMATION: Primer HM2K

<400> SEQUENCE: 5
aaaggtacca gctgtctttc tgtctgtcc                                       29

<210> SEQ ID NO 6
<211> LENGTH: 28
<212> TYPE: DNA
<213> ORGANISM: Artificial Sequence
<220> FEATURE:
<223> OTHER INFORMATION: Primer BST2B

<400> SEQUENCE: 6
atagtcatac gaagtagatg ccatccag                                        28

<210> SEQ ID NO 7
<211> LENGTH: 2144
<212> TYPE: DNA
<213> ORGANISM: Homo sapiens
<220> FEATURE:
<221> NAME/KEY: misc_feature
<222> LOCATION: (1)...(2144)
<223> OTHER INFORMATION: Nucleotide sequence coding for IRF-2 protein

<400> SEQUENCE: 7
aactgacggg ctttcatttc catttcacac accctagcaa cacttatacc ttgcggaatt      60
gtattggtag cgtgaaaaaa gcacactgag agggcaccat gccggtgaa aggatgcgca      120 tgcgcccgtg gctggaggag cagataaact ccaacacgat cccggggctc aagtggctta     180
acaaggaaaa gaagattttt cagatccccct ggatgcatgc ggctagacat gggtgggatg    240
tggaaaaaga tgcaccactc tttagaaacc gggcaatcca tacaggaaag catcaaccag     300
gagtagataa acctgatccc aaaacatgga aggcgaattt cagatgcgcc atgaattcct     360
tgcctgatat tgaagaagtc aaggataaaa gcataaagaa aggaaataat gccttcaggg    420
tctaccgaat gctgcccta tcagaacggc cttctaagaa aggaaagaaa ccaaagacag     480
```

```
aaaaagaaga caaagttaag cacatcaagc aagaaccagt tgagtcatct ctggggctta    540
gtaatggagt aagtgatctt tctcctgagt atgcggtcct gacttcaact ataaaaaatg    600
aagtggatag tacggtgaac atcatagttg taggacagtc ccatctggac agcaacattg    660
agaatcaaga gattgtcacc aatccgccag acatttgcca agttgtagag gtgaccactg    720
agagcgacga gcagccggtc agcatgagcg agctctaccc tctgcagatc tcccccgtgt    780
cttcctatgc agaaagcgaa acgactgata gtgtgcccag cgatgaagag agtgccgagg    840
ggcggccaca ctggcggaag aggaatattg aaggcaaaca gtacctcagc aacatggggga   900 ctcgaggctc ctacctgctg cccggcatgg cgtccttcgt cacttccaac aaaccggacc    960
tccaggtcac catcaaagag gagagcaatc cggtgcctta caacagctcc tggcccccctt   1020 ttcaagacct ccccctttct tcctccatga ccccagcatc cagcagcagt cggccagacc    1080
gggagacccg ggccagcgtc atcaagaaaa catcggatat cacccaggcc cgcgtcaaga    1140
gctgttaagc ctctgactct ccgcggtggt tgttgggggct tcttggcttt gttttgttgt    1200
ttgtttgtat tttatttttt tctctctgac acctatttta gacaaatcta agggaaaaag    1260
ccttgacaat agaacattga ttgctgtgtc caactccagt acctggagct tctctttaac    1320
tcaggactcc agcccattgg tagacgtgtg tttctagagc ctgctggatc tcccagggct    1380
actcactcaa gttcaaggac caacaagggc agtggaggtg ctgcattgcc tgcggtcaag    1440
gccagcaagg tggagtggat gcctcagaac ggacgagata atgtgaacta gctggaattt    1500
tttattcttg tgaatatgta cataggcagc actagcgaca ttgcagtctg cttctgcacc    1560
ttatcttaaa gcacttacag ataggccttc ttgtgatctt gctctatctc acagcacact    1620
cagcaccccc ttctctgccc attcccccagc ctctcttcct atcccatccc atcccatccc   1680
atcccatccc atcccatccc gctctttttcc tacttttcct tccctcaaag cttccattcc    1740
acatccggag gagaagaagg aaatgaattt ctctacagat gtcccatttt cagactgctt    1800 taaaaaaat ccttctaatc tgctatgctt gaatgccacg cggtacaaag gaaaaagtat      1860
catggaaata ttatgcaaat tcccagattt gaagacaaaa atactctaat tctaaccaga    1920
gcaagctttt ttatttttta tacaggggaa tatttattc aaggtaaaat tctaaataaa     1980
atataattgt tttttatctt ttctacagca aatttataat tttaagattc cttttcttgt    2040
ttatcagcag ttgttattac atccttgtgg cacattttt tttaattttg taaaggtgaa     2100
aaaagctttt atgagctcat ctagcaatca gattttcctg tgga                     2144
```

<210> SEQ ID NO 8
<211> LENGTH: 349
<212> TYPE: PRT
<213> ORGANISM: Homo sapiens
<220> FEATURE:
<221> NAME/KEY: UNSURE
<222> LOCATION: (0)...(0)
<223> OTHER INFORMATION: Amino acid sequence of IRF-2 protein

<400> SEQUENCE: 8

```
Met Pro Val Glu Arg Met Arg Met Arg Pro Trp Leu Glu Glu Gln Ile
 1               5                  10                  15

Asn Ser Asn Thr Ile Pro Gly Leu Lys Trp Leu Asn Lys Glu Lys Lys
             20                  25                  30

Ile Phe Gln Ile Pro Trp Met His Ala Ala Arg His Gly Trp Asp Val
         35                  40                  45

Glu Lys Asp Ala Pro Leu Phe Arg Asn Arg Ala Ile His Thr Gly Lys
     50                  55                  60
```

His Gln Pro Gly Val Asp Lys Pro Asp Pro Lys Thr Trp Lys Ala Asn
 65                  70                  75                  80

Phe Arg Cys Ala Met Asn Ser Leu Pro Asp Ile Glu Val Lys Asp
             85                  90                  95

Lys Ser Ile Lys Lys Gly Asn Asn Ala Phe Arg Val Tyr Arg Met Leu
            100                 105                 110

Pro Leu Ser Glu Arg Pro Ser Lys Lys Gly Lys Pro Lys Thr Glu
        115                 120                 125

Lys Glu Asp Lys Val Lys His Ile Lys Gln Glu Pro Val Glu Ser Ser
            130                 135                 140

Leu Gly Leu Ser Asn Gly Val Ser Asp Leu Ser Pro Glu Tyr Ala Val
145                 150                 155                 160

Leu Thr Ser Thr Ile Lys Asn Glu Val Asp Ser Thr Val Asn Ile Ile
                165                 170                 175

Val Val Gly Gln Ser His Leu Asp Ser Asn Ile Glu Asn Gln Glu Ile
                180                 185                 190

Val Thr Asn Pro Pro Asp Ile Cys Gln Val Val Glu Val Thr Thr Glu
            195                 200                 205

Ser Asp Glu Gln Pro Val Ser Met Ser Glu Leu Tyr Pro Leu Gln Ile
210                 215                 220

Ser Pro Val Ser Ser Tyr Ala Glu Ser Glu Thr Thr Asp Ser Val Pro
225                 230                 235                 240

Ser Asp Glu Glu Ser Ala Glu Gly Arg Pro His Trp Arg Lys Arg Asn
            245                 250                 255

Ile Glu Gly Lys Gln Tyr Leu Ser Asn Met Gly Thr Arg Gly Ser Tyr
            260                 265                 270

Leu Leu Pro Gly Met Ala Ser Phe Val Thr Ser Asn Lys Pro Asp Leu
            275                 280                 285

Gln Val Thr Ile Lys Glu Glu Ser Asn Pro Val Pro Tyr Asn Ser Ser
            290                 295                 300

Trp Pro Pro Phe Gln Asp Leu Pro Leu Ser Ser Ser Met Thr Pro Ala
305                 310                 315                 320

Ser Ser Ser Ser Arg Pro Asp Arg Glu Thr Arg Ala Ser Val Ile Lys
                325                 330                 335

Lys Thr Ser Asp Ile Thr Gln Ala Arg Val Lys Ser Cys
            340                 345

<210> SEQ ID NO 9
<211> LENGTH: 9
<212> TYPE: DNA
<213> ORGANISM: Artificial Sequence
<220> FEATURE:
<223> OTHER INFORMATION: IFN-gamma activated site (GAS) consensus
      Sequence
<220> FEATURE:
<221> NAME/KEY: variation
<222> LOCATION: (1)...(9)
<223> OTHER INFORMATION: n = any nucleotide

<400> SEQUENCE: 9 ttncnnnaa                                                                 9

<210> SEQ ID NO 10
<211> LENGTH: 13
<212> TYPE: DNA
<213> ORGANISM: Artificial Sequence
<220> FEATURE:
<223> OTHER INFORMATION: IFN-alpha stimulated repsonse element (ISRE)
      consensus sequence

```
<220> FEATURE:
<221> NAME/KEY: variation
<222> LOCATION: (1)...(13)
<223> OTHER INFORMATION: n = any nucleotide

<400> SEQUENCE: 10
ngaaanngaa act                                                            13

<210> SEQ ID NO 11
<211> LENGTH: 9
<212> TYPE: DNA
<213> ORGANISM: Homo sapiens
<220> FEATURE:
<221> NAME/KEY: unsure
<222> LOCATION: (1)...(9)
<223> OTHER INFORMATION: Gas motif sequence

<400> SEQUENCE: 11 ttcccagaa                                                                  9

<210> SEQ ID NO 12
<211> LENGTH: 13
<212> TYPE: DNA
<213> ORGANISM: Homo sapiens
<220> FEATURE:
<221> NAME/KEY: unsure
<222> LOCATION: (1)...(13)
<223> OTHER INFORMATION: ISRE motif sequence

<400> SEQUENCE: 12
ggaaactgaa act                                                            13

<210> SEQ ID NO 13
<211> LENGTH: 29
<212> TYPE: DNA
<213> ORGANISM: Artificial Sequence
<220> FEATURE:
<223> OTHER INFORMATION: ISRE-F2 probe

<400> SEQUENCE: 13
aatttctggg aaactgaaac tgaaaacct                                           29

<210> SEQ ID NO 14
<211> LENGTH: 29
<212> TYPE: DNA
<213> ORGANISM: Artificial Sequence
<220> FEATURE:
<223> OTHER INFORMATION: ISRE-F2 probe

<400> SEQUENCE: 14
aattaggttt tcagtttcag tttcccaga                                           29

<210> SEQ ID NO 15
<211> LENGTH: 36
<212> TYPE: DNA
<213> ORGANISM: Artificial Sequence
<220> FEATURE:
<223> OTHER INFORMATION: adp-1 probe

<400> SEQUENCE: 15
catggcatct acttcgtatg actattgcag agtgcc                                   36

<210> SEQ ID NO 16
<211> LENGTH: 36
<212> TYPE: DNA
<213> ORGANISM: Artificial Sequence
<220> FEATURE:
<223> OTHER INFORMATION: adp-2 probe
```

-continued

```
<400> SEQUENCE: 16
catgggcact ctgcaatagt catacgaagt agatgc                                36

<210> SEQ ID NO 17
<211> LENGTH: 29
<212> TYPE: DNA
<213> ORGANISM: Artificial Sequence
<220> FEATURE:
<223> OTHER INFORMATION: Primer HM2K

<400> SEQUENCE: 17
aaaggtacca gctgtctttc tgtctgtcc                                        29

<210> SEQ ID NO 18
<211> LENGTH: 28
<212> TYPE: DNA
<213> ORGANISM: Artificial Sequence
<220> FEATURE:
<223> OTHER INFORMATION: BST2B

<400> SEQUENCE: 18
atagtcatac gaagtagatg ccatccag                                         28

<210> SEQ ID NO 19
<211> LENGTH: 28
<212> TYPE: DNA
<213> ORGANISM: Artificial Sequence
<220> FEATURE:
<223> OTHER INFORMATION: Primer 10S

<400> SEQUENCE: 19
tttcggtacc taattaatcc tctgcctg                                         28

<210> SEQ ID NO 20
<211> LENGTH: 23
<212> TYPE: DNA
<213> ORGANISM: Artificial Sequence
<220> FEATURE:
<223> OTHER INFORMATION: GL Primer 2

<400> SEQUENCE: 20
ctttatgttt ttggcgtctt cca                                              23

<210> SEQ ID NO 21
<211> LENGTH: 30
<212> TYPE: DNA
<213> ORGANISM: Artificial Sequence
<220> FEATURE:
<223> OTHER INFORMATION: Primer HMP700

<400> SEQUENCE: 21
aaaggtacca gagtttacct ggtatcctgg                                       30

<210> SEQ ID NO 22
<211> LENGTH: 39
<212> TYPE: DNA
<213> ORGANISM: Artificial Sequence
<220> FEATURE:
<223> OTHER INFORMATION: Primer 11A

<400> SEQUENCE: 22
cagaggatta attaggtacc gaaagagagg tgggcttttt                            39

<210> SEQ ID NO 23
<211> LENGTH: 24
```

```
<212> TYPE: DNA
<213> ORGANISM: Artificial Sequence
<220> FEATURE:
<223> OTHER INFORMATION: Primer IRF2-F2

<400> SEQUENCE: 23
ttgtattggt agcgtgaaaa aagc                                          24

<210> SEQ ID NO 24
<211> LENGTH: 24
<212> TYPE: DNA
<213> ORGANISM: Artificial Sequence
<220> FEATURE:
<223> OTHER INFORMATION: Primer IRF2-R2

<400> SEQUENCE: 24
cagctagttc acattatctc gtcc                                          24

<210> SEQ ID NO 25
<211> LENGTH: 30
<212> TYPE: DNA
<213> ORGANISM: Artificial Sequence
<220> FEATURE:
<223> OTHER INFORMATION: Primer IRF2-F1

<400> SEQUENCE: 25
agagggtacc atgccggtgg aaaggatgcg                                    30

<210> SEQ ID NO 26
<211> LENGTH: 30
<212> TYPE: DNA
<213> ORGANISM: Artificial Sequence
<220> FEATURE:
<223> OTHER INFORMATION: Primer IRF2-R1

<400> SEQUENCE: 26
agtcggtacc ttaactgctc ttgacgcggg                                    30
```